(12) United States Patent
Feltin et al.

(10) Patent No.: US 9,044,400 B2
(45) Date of Patent: Jun. 2, 2015

(54) COSMETIC PRODUCT

(75) Inventors: Charlotte Feltin, Paris (FR); Audrey Valois, Villiers le Bacle (FR)

(73) Assignee: L'OREAL, Paris (FR)

( * ) Notice: Subject to any disclaimer, the term of this patent is extended or adjusted under 35 U.S.C. 154(b) by 419 days.

(21) Appl. No.: 13/510,493

(22) PCT Filed: Nov. 23, 2010

(86) PCT No.: PCT/IB2010/055370
§ 371 (c)(1),
(2), (4) Date: Jul. 11, 2012

(87) PCT Pub. No.: WO2011/064720
PCT Pub. Date: Jun. 3, 2011

(65) Prior Publication Data
US 2012/0282188 A1    Nov. 8, 2012

Related U.S. Application Data

(60) Provisional application No. 61/282,256, filed on Jan. 8, 2010.

(30) Foreign Application Priority Data

Nov. 25, 2009  (FR) ..................................... 09 58374

(51) Int. Cl.
| | | |
|---|---|---|
| *A61Q 1/02* | (2006.01) | |
| *A61Q 19/00* | (2006.01) | |
| *A61K 8/86* | (2006.01) | |
| *A61K 8/19* | (2006.01) | |
| *A61K 8/34* | (2006.01) | |
| *A61K 8/365* | (2006.01) | |
| *A61K 8/06* | (2006.01) | |
| *A61K 8/29* | (2006.01) | |

(52) U.S. Cl.
CPC ... *A61K 8/19* (2013.01); *A61K 8/06* (2013.01); *A61K 8/29* (2013.01); *A61K 8/345* (2013.01); *A61K 8/365* (2013.01); *A61K 8/86* (2013.01); *A61K 2800/222* (2013.01); *A61K 2800/31* (2013.01); *A61K 2800/43* (2013.01); *A61K 2800/436* (2013.01); *A61K 2800/88* (2013.01); *A61Q 1/02* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,472,798 A | 12/1995 | Kumazawa et al. | |
| 6,299,979 B1 | 10/2001 | Neubauer et al. | |
| 6,387,498 B1 | 5/2002 | Coulter et al. | |
| 6,491,927 B1 | 12/2002 | Arnaud et al. | ........................ 424/64 |
| 8,628,758 B2 * | 1/2014 | Ilekti et al. | ........................ 424/64 |
| 2002/0037255 A1 * | 3/2002 | Charambura et al. | ........... 424/44 |
| 2003/0031870 A1 | 2/2003 | Argoitia et al. | |
| 2007/0037727 A1 * | 2/2007 | Fiore et al. | ..................... 510/488 |

FOREIGN PATENT DOCUMENTS

| | | |
|---|---|---|
| EP | 0 542 669 A1 | 5/1993 |
| EP | 0 686 858 A2 | 12/1995 |
| EP | 0 787 730 A1 | 8/1997 |
| EP | 0 787 731 A2 | 8/1997 |
| EP | 0 806 201 A2 | 11/1997 |
| EP | 0 921 217 A1 | 6/1999 |
| EP | 1 172 091 A1 | 1/2002 |
| FR | 2 797 877 A1 | 3/2001 |
| JP | A-5-17710 | 1/1993 |
| JP | A-7-258460 | 10/1995 |
| JP | A-9-188830 | 7/1997 |
| JP | A-10-158450 | 6/1998 |
| JP | A-10-158541 | 6/1998 |
| JP | A-2001-11340 | 1/2001 |
| WO | WO 96/08537 A1 | 3/1996 |
| WO | WO 99/36477 A1 | 7/1999 |
| WO | WO 03/075884 A1 | 9/2003 |
| WO | WO 2009/100974 A1 | 8/2009 |
| WO | WO 2009/112991 A1 | 9/2009 |

OTHER PUBLICATIONS

Argoitia et al., "Pigments Exhibiting Diffractive Effects," pp. 539-545, Society of Vacuum Coaters, 45th Annual Technical Conference Proceedings, Apr. 13-18, 2002, Lake Buena Vista, Florida, USA.
Kirk-Othmer, "Fluorescent Whitening Agents," *Encyclopedia of Chemical Technology*, 4th Edition, vol. 11, 1994, pp. 227-241, A Wiley-Interscience Publication, John Wiley & Sons, New York, New York, USA.
Griffin, "Calculation of HLB Values of Non-Ionic Surfactants," *Journal of the Society of Cosmetic Chemists*, May 14, 1954, pp. 249-256.
Kirk-Othmer, "Surfactants and Detersive Systems," *Encyclopedia of Chemical Technology*, 3rd Edition, vol. 22, 1983, pp. 332-432, A Wiley-Interscience Publication, John Wiley & Sons, New York, New York, USA.
International Search Report for International Application No. PCT/IB2010/055370 mailed May 9, 2011.

* cited by examiner

*Primary Examiner* — Blessing M Fubara
*Assistant Examiner* — Jennifer A Berrios
(74) *Attorney, Agent, or Firm* — Oliff PLC

(57) ABSTRACT

A cosmetic product includes at least: a first anhydrous cosmetic composition including at least coloring particles that are solid at room temperature and atmospheric pressure, the particles being formed from: at least one hydrophilic dyestuff in a content of greater than or equal to 60% by weight relative to their total weight, at least one effervescent system in a content of less than or equal to 20% by weight relative to their total weight, at least one hydrophilic binder, and at least one dispersant that is different from the hydrophilic binder; and a second composition comprising at least one aqueous phase.

14 Claims, No Drawings

COSMETIC PRODUCT

The present invention relates to a cosmetic product, in particular a care, hygiene and/or makeup product for a keratin material, comprising at least two compositions, one comprising at least one aqueous phase, and the other being anhydrous and being able to be combined with the composition comprising at least one aqueous phase, directly by the user, for the purpose of giving it a colour personalized to the user's taste.

A product according to the invention is especially a product that is intended to be applied to a keratin material, in particular the skin.

In particular, a product according to the invention may be any type of cosmetic product such as a foundation, a face powder, an eye shadow, a concealer product, a blusher, a lipstick, a lip balm, a lip gloss, a lip pencil, an eye pencil, an eyeliner, a mascara, a body makeup product, a skin colouring product, a care product such as a care cream, a tinted cream or an antisun product.

BACKGROUND

The aspect of cosmetic products, most particularly their colour, is a determining factor for ensuring their appeal. In certain cases, and in particular in care products, in tinted creams and, generally, in all makeup products, the colour is an essential characteristic attribute sought by the consumer.

What is more, users are increasingly in search of quite specific shades that are in particular personalized to their own complexion. However, in general, conventional makeup compositions are incompatible with a personalized colour adjustment, that can be made directly a user.

The reason for this is that in order to obtain good colour properties, both as regards the visual aspect of the product itself and as regards the result after using the said product, it is necessary to ensure perfect dispersion or dissolution of the colouring starting materials. Furthermore, for certain colouring starting materials, and in particular for certain colorants that are difficult to dissolve or certain insoluble pigments, it is necessary to incorporate the constituents in their favoured phase, very often with vigorous mechanical stirring to force their wetting and/or dissolution, which moreover proves to be very costly in terms of energy and industrial machinery. In certain types of formulation, the colouring starting materials must even be prewetted or predissolved before being incorporated into the final preparation, which necessitates intermediate preparations and consequently makes shade corrections at the end of formulation difficult.

For all of the abovementioned reasons, the coloration of cosmetic products is thus usually obtained, at the industrial phase, by introducing colouring starting materials into the continuous phase of the said cosmetic products.

Consequently, the cosmetic products provided to users are usually already tinted and unsuitable for shade modification by the said users.

As a result, there is at the present time no simple and easy means for modifying the shade of a cosmetic product by a user. There is thus still a need for cosmetic compositions that allow the shades of the said cosmetic products to be easily modified.

SUMMARY

Contrary to all expectation, the inventors have discovered a means for giving conventional colouring starting materials an ability to be mixed with low mechanical stirring, and in particular manually, with cosmetic makeup and/or care products comprising at least one aqueous phase.

Advantageously, the colouring starting materials under consideration according to the invention prove to be capable of giving satisfactory colour properties while at the same time having significantly improved wetting and/or dissolution properties, in any type of aqueous phase.

DETAILED DESCRIPTION

Thus, according to one of its first aspects, a subject of the invention is a cosmetic product comprising at least:
  a first anhydrous cosmetic composition comprising at least colouring particles that are solid at room temperature and atmospheric pressure, the said particles being formed from:
    at least one hydrophilic dyestuff in a content of greater than or equal to 60% by weight relative to their total weight,
    at least one effervescent system in a content of less than or equal to 20% by weight relative to their total weight,
    at least one hydrophilic binder, and
    at least one dispersant that is different from the said hydrophilic binder; and
  a second composition comprising at least one aqueous phase.

The inventors have thus observed, unexpectedly, that colouring particles as defined above are capable of dispersing spontaneously on contact with an aqueous phase, even with low mechanical stirring.

The colouring particles may especially be in the form of solid granules or grains that are individualized at room temperature, i.e. which are in divided form. Thus, the hydrophilic dyestuff(s) may be coated and/or bound using at least the effervescent system(s), the hydrophilic binder(s) and the dispersant(s).

The hydrophilic dyestuff and the effervescent system, when they come into contact with an aqueous medium, bring about the immediate dispersion or dissolution in the said medium of the said associated hydrophilic dyestuff.

The amount of hydrophilic binder in the said particles is advantageously adjusted so as to obtain high colouring power and to avoid disrupting the sensory quality of the cosmetic products containing these particles by making them adhere to the skin and by avoiding any aggregation phenomena.

In general, this amount is small, i.e. less than or equal to 20% by weight and preferably less than or equal to 10% by weight relative to the weight of the said particles.

The proportion of effervescent system is, for its part, optimal so as to avoid giving the final product an excessively acidic nature with regard to cosmetic applications.

As regards the dispersant, its presence makes it possible to reinforce the dispersibility afforded mainly by the effervescent system, of the colouring particles in the aqueous medium.

As emerges from the foregoing, a product in accordance with the present invention has the advantage of offering its user, by providing him with a first composition according to the invention, the possibility of modifying at will and without difficulty the colour in the second associated composition, in particular a cosmetic composition, for instance a care, hygiene and/or makeup composition for a keratin material. Another advantage of the product according to the invention lies in the fact that the aqueous phase of the second composition is not necessarily its continuous phase. In other words, when this second composition is in the form of a water-in-oil (W/O) emulsion, spontaneous dispersion of the dyestuff may also be observed.

As emerges from the foregoing, the first composition may either be formed solely by the said colouring particles in accordance with the invention, or comprise colouring particles in combination with other ingredients especially as defined below.

With regard to these two alternatives, it should be noted, for the purposes of the present invention, that, firstly, a first anhydrous composition comprising a total content of greater than or equal to 98% by weight of solid colouring particles according to the invention relative to its total weight has a content of less than or equal to 0.5% by weight of water relative to its total weight, and, secondly, a first anhydrous composition comprising a total content of less than or equal to 98% by weight of solid colouring particles relative to its total weight has a content of less than or equal to 2% by weight or even less than or equal to 1% by weight of water relative to its total weight.

Preferably, an anhydrous composition according to the invention is totally free of water.

For the purposes of the present invention, the term "keratin material" is intended to cover the skin, mucous membranes such as the lips, the nails and keratin fibres, such as the eyelashes and the hair. According to one particular mode, the keratin material is the skin. According to another particular mode, the keratin material is the lips.

In the context of the present invention, the terms "anhydrous composition" and "first composition" are used without preference.

A cosmetic product according to the present invention may be in two main embodiments.

Thus, according to a first embodiment, the first composition is formed solely from colouring particles according to the invention and the second composition comprises at least one aqueous phase and is in the form of a cosmetic composition, especially for making up and/or caring for a keratin material.

According to a second embodiment, the first composition comprises colouring particles according to the invention in a total content of greater than or equal to 85% by weight relative to the total weight of the said composition and at least one non-aqueous binder, in particular in a content of less than or equal to 15% by weight relative to the total weight of the said composition. A first composition of this type is then, for the purposes of the invention, said to be formed "essentially" of colouring particles.

Irrespective of the embodiment described above, a first composition formed solely or essentially of colouring particles in accordance with the invention may be in the form of a "loose" or "compact" powder.

This aspect is especially appreciated with regard to the content in the said first composition of non-aqueous binder(s) defined below. The presence of such a non-aqueous binder is especially advantageous in that it allows the said first composition to be in the form of a compacted powder that is suited to certain embodiments of the present invention, as described below.

A first composition according to the invention, especially as defined according to the first and second embodiments described above, is intended to be mixed with the second composition combined in a product according to the invention, so as either to give this composition colouring properties in accordance with the user's desires, when the said second composition is free of dyestuff, or to modify the colour properties of this composition and in particular to alter its shade, when the said second composition is precoloured.

The user can thus personalize the final colour of the product obtained after mixing together the two compositions.

In the case of a product according to the invention, the second composition may then be in the form of a cosmetic composition, especially for caring for and/or making up a keratin material.

In the two embodiments of the first composition described above, namely a first composition formed solely or essentially from colouring particles, the first composition and the second composition are advantageously mixed together in a weight ratio ranging from 0.5/99.5 to 50/50 and preferably 1/99 to 20/80.

The cosmetic product according to the invention may, however, also be in another "additional" embodiment.

More specifically, this other embodiment of the invention combines a first anhydrous cosmetic composition comprising (i) colouring particles formed from at least the hydrophilic dyestuff(s), the effervescent system(s), the hydrophilic binder(s) and the dispersant(s) in a total content of greater than or equal to 4% by weight relative to the total weight of the said composition and (ii) at least coloured and/or uncoloured pulverant materials, optionally a non-aqueous binder, optionally also an additional ingredient chosen from surfactants, gelling agents, optionally polymers, fibres, chelating agents, active agents and fragrances, and mixtures thereof, and a second composition comprising at least one aqueous phase that is in the form of a cosmetic composition, especially for caring for and/or making up a keratin material.

According to this other embodiment of the invention, the first composition is said to be formed "partly" of colouring particles formed from at least one (or more) hydrophilic dyestuff(s), one (or more) effervescent system(s), one (or more) hydrophilic binder(s) and one (or more) dispersant(s).

As emerges from the foregoing, a first composition of this type may be in different variants.

According to a first variant, a first composition comprises colouring particles formed from at least the hydrophilic dyestuff(s), the effervescent system(s), the hydrophilic binder(s) and the dispersant(s) in a total content of greater than or equal to 20% by weight relative to its total weight, at least one coloured and/or uncoloured pulverant material and optionally at least one non-aqueous binder.

A variant of the first composition of this type is said to be "simplex".

For the purposes of the present invention, the term "coloured and/or uncoloured pulverant material" is intended to denote pigments, nacres and fillers, and mixtures thereof, in a loose form, unlike the hydrophilic dyestuff(s) that form an integral part of a mixture between the said hydrophilic dyestuff(s), the effervescent system(s), the hydrophilic binder(s) and the dispersant(s) that constitute the colouring particles in accordance with the invention.

Advantageously, a first "simplex" composition may comprise from 30% to 90% by weight and especially from 40% to 60% by weight of colouring particles in accordance with the invention, relative to its total weight.

The weight ratio of colouring particles in accordance with the invention/associated coloured and/or uncoloured pulverant material(s) generally ranges from 1/2 to 2/1 in a first simplex composition.

According to a second variant, a first "partly formed" composition comprises colouring particles formed from at least the hydrophilic dyestuff(s), the effervescent system(s), the hydrophilic binder(s) and the dispersant(s) in a total content of greater than or equal to 4% by weight relative to its total weight, at least one non-aqueous binder, at least one coloured and/or uncoloured pulverant material, and at least one additional ingredient chosen from surfactants, gelling agents, and optionally polymers, fibres, chelating agents, active agents and fragrances, and mixtures thereof.

A variant of the first composition of this type is said to be "complex".

In a first "complex" composition, the colouring particles may advantageously represent from 4% to 90% by weight, preferably from 5% to 70% by weight and better still from 10% to 50% by weight relative to the total weight of the said composition.

A first "complex" composition may especially be in the form of a solid anhydrous makeup composition per se, and more particularly in the form of a foundation, a face powder, an eye shadow, a blusher or a mascara, and more particularly a foundation, and the second composition may then comprise water in a content of greater than 80% by weight relative to the total weight of the said second composition.

According to this additional embodiment, a first "simplex" composition and a second composition forming a product according to the invention are advantageously mixed together in a weight ratio ranging from 3/97 to 50/50.

According to this additional embodiment, a first "complex" composition and a second composition forming a product according to the invention are advantageously mixed together in a weight ratio ranging from 90/10 to 10/90.

Thus, according to another of its aspects, the present invention also relates to a cosmetic product comprising at least:
(i) a first composition comprising colouring particles formed from at least the hydrophilic dyestuff(s), the effervescent system(s), the hydrophilic binder(s) and the dispersant(s) in a total content of greater than or equal to 98% by weight relative to the total weight of the said first composition, and
a second composition comprising at least one aqueous phase in the form of a cosmetic composition, especially for caring for and/or making up a keratin material.

According to another of its aspects, the invention is also directed towards a cosmetic product comprising at least:
(ii) a first composition comprising colouring particles formed from at least the hydrophilic dyestuff(s), the effervescent system(s), the hydrophilic binder(s) and the dispersant(s) in a total content of greater than or equal to 85% by weight relative to the total weight of the said first composition and at least one non-aqueous binder, in particular in a content of less than or equal to 15% by weight relative to the total weight of the said first composition, and
a second composition comprising at least one aqueous phase in the form of a cosmetic composition, especially for caring for and/or making up a keratin material.

According to yet another of its aspects, the invention is also directed towards a cosmetic product comprising at least:
(iii) a first composition comprising colouring particles formed from at least the hydrophilic dyestuff(s), the effervescent system(s), the hydrophilic binder(s) and the dispersant(s) in a total content of greater than or equal to 20% by weight relative to its total weight, at least one coloured and/or uncoloured pulverant material, chosen especially from pigments, nacres and fillers, and mixtures thereof, and optionally at least one non-aqueous binder, and
a second composition comprising at least one aqueous phase in the form of a cosmetic composition, especially a composition for caring for and/or making up a keratin material.

According to yet another of its aspects, the invention is also directed towards a cosmetic product comprising at least:
(iv) a first composition comprising colouring particles formed from at least the hydrophilic dyestuff(s), the effervescent system(s), the hydrophilic binder(s) and the dispersant(s) in a total content of greater than or equal to 4% by weight relative to the total weight of the said first composition, at least one non-aqueous binder, at least one coloured and/or uncoloured pulverant material, and at least one additional ingredient chosen from surfactants, gelling agents, and optionally polymers, fibres, chelating agents, active agents and fragrances, and mixtures thereof, and
a second composition comprising at least water in a content of greater than 80% by weight relative to the total weight of the said second composition.

A subject of the present invention is also a cosmetic process comprising at least the steps consisting in:
(i) providing at least a first anhydrous composition according to the invention;
(ii) mixing at least part of the said first composition with at least a second composition comprising at least one aqueous phase; and
(iii) applying at least part of the mixture obtained in (ii) to the surface of a keratin material.

According to one particular embodiment, steps (ii) and (iii) of the process described above may be performed simultaneously.

Advantageously, the first composition under consideration in the process according to the invention is formed solely or essentially from colouring particles formed from at least the hydrophilic dyestuff(s), the effervescent system(s), the hydrophilic binder(s) and the dispersant(s), as defined above.

According to one particular embodiment, the first and second compositions under consideration according to the invention are packaged separately in the same packaging article.

In this respect, a subject of the invention is also a packaging assembly comprising at least:
a first compartment comprising at least a first anhydrous composition in accordance with the invention;
a second compartment comprising at least a second composition comprising at least one aqueous phase, the said second compartment being, prior to the use of the assembly, sealably isolated from the first; and
optionally, means for, for example in response to a command, allowing communication between the first and second compartments.

According to one particular embodiment, the packaging assembly defined above may also comprise a means that is suitable for dispensing or applying at least part of the mixture obtained by placing the said first and second compartments in communication on a keratin material.

According to one preferred variant, the packaging assembly contains a first composition formed solely or essentially from colouring particles formed from at least the hydrophilic dyestuff(s), the effervescent system(s), the hydrophilic binder(s) and the dispersant(s), as defined above.

It is understood that a packaging assembly may comprise several first compositions, which are different from each other, especially in the nature and/or amount of their respective colouring particles.

According to this embodiment, the user then has at his disposal an even wider range of choice in terms of colour effect.

Similarly, a packaging assembly may also comprise several second compositions.

For example, these second compositions may differ from each other in their galenical formulation, one being, for example, more particularly intended for forming a lip gloss and the other a foundation or a fluid makeup powder.

The user then has the possibility via the use of a single first composition, of being able to adjust to his desire the shade of two types of cosmetic formulation, which are especially intended for different keratin materials.

Needless to say, the two options under consideration above may be envisaged in a single packaging.

The present invention is also directed towards an article combining a range of first compositions in accordance with the invention which differ from each other in their nature and/or their proportion of colouring particles according to the invention.

The user, having at his disposal such an article, may as he desires give a colour to or modify the colour of a second composition, by benefiting from a wide range of colours.

A subject of the invention is also the cosmetic use of at least a first anhydrous composition in accordance with the invention for tinting or modifying a colour property of a second composition comprising at least one aqueous phase, especially a cosmetic composition.

A—First Composition

As emerges from the foregoing, a first composition according to the invention comprises at least colouring particles that are solid at room temperature and atmospheric pressure, the said particles being formed from at least one hydrophilic dyestuff in a content of greater than or equal to 60% by weight relative to the total weight of the said colouring particles, at least one effervescent system in a content of less than or equal to 20% by weight relative to the total weight of the said colouring particles, at least one hydrophilic binder, and at least one dispersant that is different from the said hydrophilic binder.

The different variants of first compositions arising from the present invention are described above.

The description that follows details the constituent ingredients of the said colouring particles in accordance with the invention.

I—Hydrophilic Dyestuff

For the purposes of the invention, the term "hydrophilic" means that the material under consideration has affinity for water. This affinity is reflected either by solubility properties or by wettabililty properties, manifested by the said material on contact with water, i.e. by homogeneous dispersion of the said material within an aqueous phase.

For the purposes of the invention, the term "wettability" means the ability of a surface to be wetted by a given material, in particular by water.

In general, when a liquid is placed in contact with the surface of a solid, it forms a contact angle of the first on the second. When the wetting is perfect, the contact angle becomes zero. In this case, the adhesion energy is maximal.

For a given liquid-solid system, the wetting depends on the pressure, the temperature and the hygrometry.

The wetting may especially be measured by contact-angle tensiometry, by means, for example, of a DAT 1100 tensiometer sold by the company Fibro (Sweden).

A protocol for evaluating the wetting of a hydrophilic dyestuff of the invention may especially be as follows.

The hydrophilic dyestuffs are compacted, for example with a force of 10 tons/cm$^2$, to form a flat surface prior to measurement. The contact angle is then measured 0.1 s after placing a drop of water on the surface.

When the hydrophilic dyestuffs cannot be compacted, the wetting may be measured by capillary rise using the Washburn equation. A Kruss K12 tensiometer will then be used, for example, by placing the hydrophilic dyestuffs in a Kruss FL12 sample holder.

The hydrophilic dyestuffs in accordance with the invention especially have a contact angle of less than 90°, preferably less than 70° and preferably less than 50°.

The hydrophilic dyestuffs in accordance with the invention, when they are in the form of particles, especially have a mean particle size of between 0.5 and 100 µm and preferably between 1 and 100 µm.

Preferably, the solid colouring particles in accordance with the invention comprise from 60% to 95% by weight, preferably from 65% to 90% by weight and better still from 70% to 85%, or even from 75% to 85% by weight, of hydrophilic dyestuff(s) relative to the total weight of the said colouring particles.

For the purposes of the present invention, these hydrophilic dyestuffs are more particularly chosen from:
water-soluble dyes;
pigments;
nacres;
particles with a metallic glint;
polymeric particles;
particles with an optical effect; and
mixtures thereof.

According to one preferred mode of the invention, the hydrophilic dyestuffs are chosen from pigments, and especially mineral pigments. They are more particularly chosen from iron oxides, titanium dioxide, pigments with an optical effect, especially with an interference effect (or iridescent effect) such as mica-titanium oxide, and mixtures thereof. Iron oxides that may especially be used include yellow, red and black iron oxides.

For the purposes of the invention, the term "water-soluble dye" means any natural or synthetic, generally organic compound, which is soluble in an aqueous phase or water-miscible solvents and which is capable of colouring.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanine (beetroot), carmine, copper chlorophylline, methylene blue, anthocyanins (enocianin, black carrot, hibiscus and elder), caramel and riboflavin.

Mention may also be made of juglone, lawsone, fermented soybean extracts, algal extracts, fungal extracts and microorganism extracts, flavylium salts not substituted in position 3, for instance those described in patent EP 1 172 091, extracts of *Gesneria fulgens, Blechum procerum* and *Saxifraga* and pigments that may be obtained via extraction with an organic or aqueous-organic solvent of a culture medium of micromycetes of the *Monascus monascus* type.

As regards the pigments, nacres, particles with a metallic glint and polymeric particles, they may be compounds that naturally have the required hydrophilic properties.

However, any pigment, nacre, particle with a metallic glint or polymeric particle that satisfies the required hydrophilic nature of the invention by means of a suitable surface treatment, for example using a hydrophilic organic agent, is also suitable for use in the invention.

Generally, a hydrophilic organic agent for surface-treating a material in order to optimize its dispersion in aqueous medium is more particularly chosen from biological polymers, carbohydrates, polysaccharides, polyacrylates and polyethylene glycol derivatives.

The materials thus treated may, in the absence of being soluble in a solvent medium, such as water, be dispersible therein.

As examples of biological polymers for coating the dyestuffs to be dissolved according to the invention, mention may be made of polymers based on monomers of carbohydrate type. More particularly, mention may be made of biosaccharide gum, chitosans and derivatives thereof, such as butoxy chitosan, carboxymethyl chitosan, carboxybutyl chitosan, chitosan gluconate, chitosan adipate, chitosan glycolate, chitosan lactate, etc., chitins and derivatives thereof, such as carboxymethyl chitin, chitin glycolate; cellulose and derivatives thereof such as cellulose acetate; microcrystalline cellulose; distarch phosphate; sodium hyaluronate; soluble proteoglycans; galacto-arabinans; glycosaminoglycans; glycogen; sclerotium gum; dextran; starch and derivatives thereof; and mixtures thereof.

The term "pigments" should be understood as meaning white or coloured, mineral or organic particles that are insoluble in an aqueous solution, which are intended to colour and/or opacify the resulting film.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof. According to one preferred mode, titanium oxides and dioxides and iron oxides (especially yellow, black or red iron oxide), and mixtures thereof, will be used.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment consisting of silica microspheres containing yellow iron oxide.

Among the organic pigments that may be used in the invention, mention may be made of carbon black, pigments of D & C type, lakes based on cochineal carmine or on barium, strontium, calcium or aluminium, or alternatively the diketopyrrolopyrroles (DPP) described in documents EP-A-0 542669, EP-A-0 787730, EP-A-0 787731 and WO-A-96/08537.

Advantageously, the pigments in accordance with the invention are iron oxides and/or titanium dioxides.

The term "nacres" should be understood as meaning coloured particles of any form, which may or may not be iridescent, especially produced by certain molluscs in their shell, or alternatively synthesized, and which have a colour effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the commercially available nacres that may be mentioned are the nacres Timica, Flamenco and Duochrome (on mica base) sold by the company Engelhard, the Timiron nacres sold by the company Merck, the Prestige nacres on mica base sold by the company Eckart and the Sunshine nacres on synthetic mica base sold by the company Sun Chemical.

The nacres may more particularly have a yellow, pink, red, bronze, orange, brown, gold and/or coppery colour or glint.

As illustrations of nacres that may be used in the context of the present invention, mention may be made of gold-coloured nacres sold especially by the company Engelhard under the name Brillant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nu-antique copper 340XB (Cloisonne) and Brown CL4509 (Chromalite); the nacres with a copper glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red-tinted nacres with a golden glint sold especially by the company Engelhard under the name Sunstone G012 (Gemtone); the pink nacres sold especially by the company Engelhard under the name Tan opale G005 (Gemtone); the black nacres with a golden glint sold especially by the company Engelhard under the name Nu antique bronze 240 AB (Timica); the blue nacres sold especially by the company Merck under the name Matte blue (17433) (Microna); the white nacres with a silvery glint sold especially by the company Merck under the name Xirona Silver; and the golden-green pinkish-orange nacres sold especially by the company Merck under the name Indian summer (Xirona), and mixtures thereof.

The term "particles with a metallic glint", within the meaning of the present invention, denotes particles whose nature, size, structure and surface state allow them to reflect the incident light, especially in a non-iridescent manner.

Particles with a substantially flat outer surface are also suitable, since they can, if their size, structure and surface state allow it, more easily give rise to a strong specular reflection, which may then be termed a mirror effect.

The particles with a metallic glint that may be used in the invention may, for example, reflect light in all the components of the visible region without significantly absorbing one or more wavelengths. The spectral reflectance of these particles may, for example, be greater than 70% and better still at least 80%, or even 90% or 95%, in the range 400-700 nm.

These particles generally have a thickness of less than or equal to 1 µm, especially less than or equal to 0.7 µm and in particular less than or equal to 0.5 µm.

The particles with a metallic glint that may be used in the invention are in particular chosen from:
  particles of at least one metal and/or of at least one metal derivative,
  particles comprising a monomaterial or multimaterial organic or mineral substrate, at least partially coated with at least one layer with a metallic glint comprising at least one metal and/or at least one metal derivative, and mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se and mixtures or alloys thereof. Ag, Au, Cu, Al, Zn, Ni, Mo and Cr, and mixtures or alloys thereof (for example bronzes and brasses) are preferred metals.

The term "metal derivatives" is intended to denote compounds derived from metals, especially oxides, fluorides, chlorides and sulfides.

Among the metal derivatives that may be present in the said particles, mention may be made especially of metal oxides, for instance titanium oxide, especially $TiO_2$, iron oxide, especially $Fe_2O_3$, tin oxide, chromium oxide, barium sulfate and the following compounds: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

Illustrations of these particles that may be mentioned include aluminium particles, such as those sold under the names Starbrite 1200 EAC® by the company Silberline and Metalure® by the company Eckart.

Mention may also be made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver® from the company Eckart, and metal alloy particles, for instance the silica-coated bronze (alloy of copper and zinc) powders sold under the name Visionaire Bright Natural Gold® from the company Eckart.

According to a second variant, these particles may be particles comprising a substrate, which thus have a multilayer structure, for example a two-layer structure. This substrate may be organic or mineral, natural or synthetic, monomaterial or multimaterial, solid or hollow. When the substrate is synthetic, it may be made in a form promoting the formation of a reflective surface after coating, especially after depositing a layer of materials with a metallic glint. The substrate may, for example, have a flat surface and the layer of materials with a metallic glint may have a substantially uniform thickness.

The substrate may be chosen in particular from the metals and metal derivatives as mentioned above, and also from glasses, ceramics, aluminas, silicas, silicates and especially aluminosilicates and borosilicates, synthetic mica such as fluorophlogopite, and mixtures thereof, this list not being limiting.

The layer with a metallic glint may totally or partially coat the substrate and this layer may be at least partially covered with a layer of another material, for example a transparent material especially as mentioned above. According to one particular embodiment, this layer with a metallic glint totally coats the substrate directly or indirectly, i.e. with interposition of at least one metallic or non-metallic intermediate layer.

The metals or metal derivatives that may be used in the reflective coat are as defined above. For example, it may be formed from at least one metal chosen from silver, aluminium, chromium, nickel, molybdenum, gold, copper, tin and magnesium, and mixtures (alloys) thereof. Silver, chromium, nickel and molybdenum, and mixtures thereof, are more particularly used.

As illustrations of particles of this second type, mention may be made more particularly of:

Glass particles coated with a metallic layer, especially those described in documents JP-A-09188830, JP-A-10158450, JP-A-10158541, JP-A-07258460 and JP-A-05017710.

As illustrations of these particles comprising a glass substrate, mention may be made of those coated, respectively, with silver, gold or titanium, in the form of platelets, sold by the company Nippon Sheet Glass under the name Microglass Metashine. Particles comprising a silver-coated glass substrate, in the form of platelets, are sold under the name Microglass Metashine REFSX 2025 PS by the company Toyal. Particles comprising a glass substrate coated with nickel/chromium/molybdenum alloy are sold under the name Crystal Star GF 550 and GF 2525 by this same company. Those coated either with brown iron oxide or with titanium oxide, tin oxide or a mixture thereof, for instance those sold under the name Reflecks® by the company Engelhard or those sold under the name Metashine MC 2080GP by the company Nippon Sheet Glass.

These metal-coated glass particles may be coated with silica, for instance those sold under the name Metashine series PSS1 or GPS1 by the company Nippon Sheet Glass.

Particles comprising a spherical glass substrate optionally coated with a metal, especially those sold under the name Prizmalite Microsphere by the company Prizmalite Industries.

Pigments of the Metashine 1080R range sold by the company Nippon Sheet Glass Co. Ltd are also suitable for the invention. These pigments, more particularly described in patent application JP 2001-11340, are C-Glass glass flakes comprising 65% to 72% $SiO_2$, coated with a layer of titanium oxide of rutile type ($TiO_2$). These glass flakes have a mean thickness of 1 micron and a mean size of 80 microns, i.e. a mean size/mean thickness ratio of 80. They have blue, green or yellow glints or a silver shade depending on the thickness of the $TiO_2$ layer.

Particles comprising a silver-coated borosilicate substrate, also known as "white nacres".

Particles comprising a metal substrate such as aluminium, copper or bronze, in the form of platelets, are sold under the trade name Starbrite by the company Silberline and under the name Visionaire by the company Eckart.

Particles comprising a synthetic mica substrate coated with titanium dioxide, and for example particles with a size of between 80 and 100 μm, comprising a synthetic mica (fluorophlogopite) substrate coated with titanium dioxide representing 12% of the total weight of the particle, sold under the name Prominence by the company Nihon Koken.

The particles with a metallic glint may also be chosen from particles formed from a stack of at least two layers with different refractive indices. These layers may be of polymeric or metallic nature and may especially include at least one polymer layer.

Thus, the particles with a metallic effect may be particles derived from a multilayer polymer film.

The choice of materials intended to constitute the various layers of the multilayer structure is obviously made so as to give the particles thus formed the desired metallic effect.

Such particles are especially described in WO 99/36477, U.S. Pat. Nos. 6,299,979 and 6,387,498 and more particularly identified below in the goniochromatic section.

For the purposes of the invention, the term "particles with an optical effect" is intended to denote any compound such as diffracting pigments, goniochromatic colouring agents and optical brighteners.

Preferably, particles with an optical effect that are solid at room temperature and atmospheric pressure are suitable for use in the invention.

For the purposes of the present invention, the term "diffractive pigment" denotes a pigment capable of producing a colour variation according to the angle of observation when lit with white light, on account of the presence of a structure that diffracts light.

A diffractive pigment may comprise a diffracting network capable, for example, of diffracting an incident monochromatic light ray in defined directions.

The diffraction network may comprise a periodic unit, especially a line, the distance between two adjacent units being of the same order of magnitude as the wavelength of the incident light.

When the incident light is polychromatic, the diffraction network will separate the various spectral components of the light and produce a rainbow effect.

Reference may appropriately be made regarding the structure of diffractive pigments to the article "*Pigments Exhibiting Diffractive Effects*" by Alberto Argoitia and Matt Witzman, 2002, Society of Vacuum coaters, 45th Annual Technical Conference Proceedings 2002.

The diffractive pigment may be made with units having different profiles, especially triangular, symmetrical or non-symmetrical, in gaps, of constant or non-constant width, or sinusoidal.

The spatial frequency of the network and the depth of the units will be chosen as a function of the degree of separation of the various orders desired. The frequency may range, for example, between 500 and 3000 lines per mm.

Preferably, the particles of the diffractive pigment each have a flattened form, and are especially in the form of platelets.

The same pigment particle may comprise two crossed, perpendicular or non-perpendicular diffraction networks.

A possible structure for the diffractive pigment may comprise a layer of a reflective material, covered at least on one side with a layer of a dielectric material. The latter material may give the diffractive pigment better rigidity and durability. The dielectric material may thus be chosen, for example, from the following materials: $MgF_2$, $SiO_2$, $Al_2O_3$, $AlF_3$, $CeF_3$, $LaF_3$, $NdF_3$, $SmF_2$, $BaF_2$, $CaF_2$, LiF and combinations thereof. The reflective material may be chosen, for example, from metals and alloys thereof, and also from non-metallic reflective materials. Among the metals that may be used, mention may be made of Al, Ag, Cu, Au, Pt, Sn, Ti, Pd, Ni, Co, Rd, Nb and Cr, and compounds, combinations or alloys thereof. Such a reflective material may, by itself, constitute the diffractive pigment, which will then be monolayer.

As a variant, the diffractive pigment may comprise a multilayer structure comprising a core of a dielectric material covered with a reflective layer at least on one side, or even totally encapsulating the core. A layer of a dielectric material may also cover the reflective layer(s). The dielectric material used is then preferably mineral, and may be chosen, for example, from metal fluorides, metal oxides, metal sulfides, metal nitrides, and metal carbides, and combinations thereof. The dielectric material may be in crystalline, semi-crystalline or amorphous form. In this configuration, the dielectric material may be chosen, for example, from the following materials: $MgF_2$, SiO, $SiO_2$, $Al_2O_3$, $TiO_2$, WO, AN, BN, $B_4C$, WC, TiC, TiN, $N_4Si_3$, ZnS, glass particles and carbons of diamond type, and combinations thereof.

The diffractive pigment used may be chosen especially from those described in the American patent application US 2003/0 031 870 published on 13 Feb. 2003.

A diffractive pigment may comprise, for example, the following structure: $MgF_2/Al/MgF_2$, a diffractive pigment having this structure being sold under the name Spectraflair 1400 Pigment Silver by the company Flex Products, or Spectraflair 1400 Pigment Silver FG. The weight proportion of $MgF_2$ may be between 80% and 95% of the total weight of the pigment.

For the purposes of the invention, a "goniochromatic colouring agent" allows a colour change, also known as a "colour flop", to be observed as a function of the angle of observation, greater than that which may be encountered with nacres. One or more goniochromatic colouring agents may be used simultaneously.

The goniochromatic colouring agent may be chosen so as to present a relatively large colour change with the angle of observation.

The goniochromatic colouring agent may thus be chosen such that a colour difference ΔE of the cosmetic composition, measured in the CIE 1976 colorimetric space, of at least 2 may be observed for a variation of the angle of observation of between 0° and 80° under illumination at 45°.

The goniochromatic colouring agent may also be chosen such that a variation Dh of the hue angle of the cosmetic composition, in the CIE 1976 plane, of at least 30° or even at least 40° or at least 60°, or even at least 100°, may be observed for an illumination at 45° and a variation of the angle of observation of between 0° and 80°.

The goniochromatic colouring agent may be chosen, for example, from multilayer interference structures and liquid-crystal colouring agents.

In the case of a multilayer structure, it may comprise, for example, at least two layers, each layer, which may or may not be independent of the other layer(s), being made, for example, from at least one material chosen from the group consisting of the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, and alloys, polymers and combinations thereof.

The multilayer structure may or may not have, relative to a central layer, symmetry in the chemical nature of the stacked layers.

Examples of symmetrical multilayer interference structures that may be used in the compositions prepared in accordance with the invention are, for example, the following structures: $Al/SiO_2/Al/SiO_2/Al$, pigments having this structure being sold by the company Dupont de Nemours; $Cr/MgF_2/Al/MgF_2/Cr$, pigments having this structure being sold under the name Chromaflair by the company Flex; $MoS_2/SiO_2/Al/SiO_2/MoS_2$; $Fe_2O_3/SiO_2/Al/SiO_2/Fe_2O_3$, and $Fe_2O_3/SiO_2/Fe_2O_3/SiO_2/Fe_2O_3$, pigments having these structures being sold under the name Sicopearl by the company BASF; $MoS_2/SiO_2/mica-oxide/SiO_2/MoS_2$; $Fe_2O_3/SiO_2/mica-oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by the company Merck (Darmstadt). By way of example, these pigments may be pigments of silica/titanium oxide/tin oxide structure sold under the name Xirona Magic by the company Merck, pigments of silica/brown iron oxide structure sold under the name Xirona Indian Summer by the company Merck, and pigments of silica/titanium oxide/mica/tin oxide structure sold under the name Xirona Caribbean Blue by the company Merck. Mention may also be made of the Infinite Colors pigments from the company Shiseido. Depending on the thickness and the nature of the various layers, different effects are obtained. Thus, with the $Fe_2O_3/SiO_2/Al/SiO_2/Fe_2O_3$ structure, the colour changes from green-golden to red-grey for $SiO_2$ layers of 320 to 350 nm; from red to golden for SiO$_2$ layers of 380 to 400 nm; from violet to green for SiO$_2$ layers of 410 to 420 nm; from copper to red for SiO$_2$ layers of 430 to 440 nm.

Goniochromatic colouring agents with a multilayer structure comprising an alternation of polymeric layers may also be used.

As illustrations of the materials that can constitute the various layers of the multilayer structure, it is possible to mention, this list not being limiting: polyethylene naphthalate (PEN) and its isomers, for example 2,6-, 1,4-, 1,5-, 2,7- and 2,3-PEN, polyalkylene terephthalates, polyimides, polyetherimides, atactic polystyrenes, polycarbonates, polyalkyl methacrylates and polyalkyl acrylates, syndiotactic polystyrene (sPS), syndiotactic poly-α-methylstyrenes, syndiotactic polydichlorostyrene, copolymers and blends of these polystyrenes, cellulose derivatives, polyalkylene polymers, fluoropolymers, chloropolymers, polysulfones, polyether sulfones, polyacrylonitriles, polyamides, silicone resins, epoxy resins, polyvinyl acetate, polyetheramides, ionomeric resins, elastomers and polyurethanes. Copolymers are also suitable, for example copolymers of PEN (for example copolymers of 2,6-, 1,4-, 1,5-, 2,7-, and/or 2,3-naphthalenedicarboxylic acid or the esters thereof with (a) terephthalic acid or its esters; (b) isophthalic acid or its esters; (c) phthalic acid or its esters; (d) alkane glycols; (e) cycloalkane glycols (for example cyclohexanedimethanol diol); (f) alkanedicarboxylic acids; and/or (g) cycloalkanedicarboxylic acids, polyalkylene terephthalate copolymers and styrene copolymers. In addition, each individual layer may include blends of two or more of the above polymers or copolymers. The choice of materials intended to constitute the various layers of the multilayer structure is, of course, made so as to give the particles thus formed the desired optical appearance.

As examples of pigments with a polymeric multilayer structure, mention may be made of those sold by the company 3M under the name Color Glitter.

The liquid-crystal colouring agents comprise, for example, silicones or cellulose ethers onto which are grafted mesomorphic groups.

Examples of liquid-crystal goniochromatic particles that may be used include, for example, those sold by the company Chemx and also the products sold under the name Helicone® HC by the company Wacker.

These agents may also be in the form of dispersed goniochromatic fibres. Such fibres may, for example, have a size of between 50 μm and 700 μm, for example about 300 μm. Interference fibres with a multilayer structure may be used in particular. Fibres with a multilayer structure of polymers are described especially in documents EP-A-0 921 217, EP-A-0 686 858 and U.S. Pat. No. 5,472,798. The multilayer structure may comprise at least two layers, each layer, which may or may not be independent of the other layer(s), being made of at least one synthetic polymer. The polymers present in the fibres may have a refractive index ranging from 1.30 to 1.82 and better still ranging from 1.35 to 1.75. The polymers that are preferred for making the fibres are polyesters such as polyethylene terephthalate, polyethylene naphthalate, polycarbonate; acrylic polymers such as polymethyl methacrylate; polyamides.

Goniochromatic fibres with a polyethylene terephthalate/nylon-6 two-layer structure are sold by the company Teijin under the name Morphotex.

In one variant, this goniochromatic colouring agent may be combined with at least one diffractive pigment.

The combination of these two materials results in a composition or a film that has increased colour variability, and thus which is capable of allowing an observer to see a colour change, or even a colour movement, under various observation and lighting conditions.

The weight ratio of the diffractive pigment relative to the goniochromatic colouring agent is preferably between 85/15 and 15/85, better still between 80/20 and 20/80 and better still between 60/40 and 40/60, for example about 50/50. Such a ratio is favourable towards obtaining a strong rainbow effect and a strong goniochromatic effect.

"Optical brighteners" are compounds that are well known to those skilled in the art. Such compounds are in particular described in "Fluorescent Whitening Agent, Encyclopedia of Chemical Technology, Kirk-Othmer", Vol. 11, pp. 227-241, 4th Edition, 1994, Wiley. They may be defined more particularly as compounds that absorb essentially in the UVA range between 300 and 390 nm and re-emit essentially between 400 and 525 nm. Among the optical brighteners that may be mentioned more particularly are stilbene derivatives, in particular polystyrylstilbenes and triazinestilbenes, coumarin derivatives, in particular hydroxycoumarin and amino coumarins, oxazole, benzoxazole, imidazole, triazole and pyrazo line derivatives, pyrene derivatives and porphyrin derivatives, and mixtures thereof. Such compounds are widely commercially available.

Mention may be made, for example, of: the naphthotriazole stilbene derivative sold under the trade name Tinopal GS, disodium 4,4'-distyrylbiphenylsulfonate (CTFA name: disodium distyrylbiphenyl disulfonate) sold under the trade name Tinopal CBS-X, the cationic aminocoumarin derivative sold under the trade name Tinopal SWN Conc., the sodium 4,4'-bis[(4,6-dianilino-1,3,5-triazin-2-yl)amino]stilbene-2,2'-disulfonate sold under the trade name Tinopal SOP, the 4,4'-bis[(4-anilino-6-bis(2-hydroxyethyl)amino-1,3,5-triazin-2-yl)amino]stilbene-2,2'-disulfonic acid sold under the trade name Tinopal UNPA-GX, the 4,4'-bis[anilino-6-morpholine-1,3,5-triazin-2-yl)amino]stilbene sold under the trade name Tinopal AMS-GX, the disodium 4,4'-bis[(4-anilino-6-(2-hydroxyethyl)methylamino-1,3,5-triazin-2-yl)amino]stilbene-2,2'-sulfonate sold under the trade name Tinopal 5BM-GX, all by the company Ciba Spéecialités Chimiques, 2,5-thiophenediylbis(5-tert-butyl-1,3-benzoxazole) sold under the trade name Uvitex OB by the company Ciba, the anionic derivative of diaminostilbene as a dispersion in water, sold under the trade name Leucophor BSB Liquid by the company Clariant, and the optical brightener lakes sold under the trade name Covazur by the company Wackherr.

The optical brighteners that may be used in the present invention may also be in the form of copolymers, for example acrylates and/or methacrylates, grafted with optical brightener groups as described in patent application FR 99/10942.

In particular, the fibres coated with optical brightener as sold by the company LCW under the trade reference Fiberlon 54 ZO$_3$, with a length of about 0.4 mm and a yarn count of 0.5 denier, may be used.

II—Effervescent System

For the purposes of the present invention, the term "effervescent system" is intended to denote an acid/base couple.

An "acid/base couple" refers to an acid and a base that are capable of interacting with each other, at room temperature and atmospheric pressure.

This reactivity may especially be reflected by the manifestation of effervescent properties, especially on contact with an aqueous medium.

In particular, the proportions of acid and base will correspond substantially to the stoichiometric equilibrium of the effervescent reaction between the two constituents.

Thus, the base is more particularly a substance that is capable of generating a gas, $CO_2$, on contact with the associated acid and water.

(Bi)carbonates or an anhydrous salt thereof, phosphates, polyphosphates, alkali metal peroxides, such as sodium perborate and sodium percarbonate, and azides, and mixtures thereof, are most particularly suitable in this respect.

According to one preferred embodiment, the base is represented by an alkali metal or alkaline-earth metal (bi)carbonate that is chosen for its reactivity with regard to the associated acid. Its choice clearly falls within the competence of a person skilled in the art.

Among the examples of (bi)carbonate compounds that may be used in the context of the present invention, mention may be made especially of sodium (bi)carbonate, potassium (bi)carbonate, magnesium (bi)carbonate and calcium (bi)carbonate, and mixtures thereof.

Sodium (bi)carbonate and potassium (bi)carbonate are most particularly suitable for use in the invention.

Advantageously, a base in accordance with the invention is sodium bicarbonate.

Its amount is also adjusted with regard to that of the associated acid.

As regards the acid component, it is preferably an organic acid.

Among the organic acids that may be used in a solid anhydrous composition according to the invention, any organic acid that is compatible with cosmetic topical use will be chosen, especially $C_2$ to $C_{22}$ carboxylic acids. The acid in accordance with the invention must be soluble in water at room temperature.

As examples of acids that are suitable in the context of the present invention, mention may be made especially of carboxylic acids, diacids and triacids, especially a- and β-hydrocarboxylic acids.

According to one preferred embodiment, an acid that is suitable for use in the invention is an organic acid that may be chosen especially from acetic acid, citric acid, lactic acid, gluconic acid, tartaric acid, ascorbic acid, succinic acid, malic acid, malonic acid, fumaric acid, glutaric acid, adipic acid, pimelic acid, maleic acid, phthalic acid, glutamic acid, aspartic acid, glycolic acid, tartronic acid, hydroxybenzoic acid, salicylic acid, tropic acid, cinnamic acid, phenylacetic acid, nicotinic acid, sorbic acid and trimellitic acid, and mixtures thereof.

According to a more particularly preferred embodiment, the organic acid is chosen from acetic acid, citric acid, lactic acid, tartaric acid, gluconic acid, adipic acid and malic acid, and mixtures thereof.

Advantageously, the organic acid in accordance with the invention is citric acid.

According to one preferred embodiment, the acid/base couple is the citric acid/sodium (bi)carbonate couple.

According to one preferred embodiment, the mole ratio between the acid and the base ranges from 0.5 to 10, in particular from 1 to 6 and preferably from 1.5 to 3.

The colouring particles that are solid at room temperature and atmospheric pressure in accordance with the invention may comprise from 1% to 20% by weight, preferably from 5% to 15% by weight and better still from 8% to 12% by weight of effervescent system(s), relative to their total weight.

III—Hydrophilic Binder

For the purposes of the present invention, the term "hydrophilic binder" is intended to denote any compound chosen from $C_4$-$C_{32}$ polyols and polyoxyethylenated ethers.

Hydrophilic binders that are solid at room temperature and atmospheric pressure, and which preferably have a melting point ranging from 30° C. to 120° C. and preferably from 40° C. to 100° C., are more particularly suitable for use in the invention.

The solid hydrophilic binders in accordance with the invention have rapid dissolution properties in aqueous medium, i.e. the dissolution takes place over a maximum period of 30 minutes at room temperature and atmospheric pressure in water, at a binder concentration of at least 0.1% by weight, preferably of at least 0.5% by weight and better still of at least 1% by weight.

Preferably, the solid colouring particles in accordance with the invention may comprise from 1% to 20% by weight, preferably from 2% to 10% by weight and better still from 4% to 8% by weight, or even from 5% to 8% by weight, of hydrophilic binder(s), relative to their total weight.

For the purposes of the present invention, the term "polyol" should be understood as meaning any organic molecule comprising at least two free hydroxyl groups.

A polyol that is suitable for use in the invention may be a compound of linear, branched or cyclic, saturated or unsaturated alkyl type, bearing on each alkyl chain at least two —OH functions, in particular at least three —OH functions and more particularly at least four —OH functions.

The polyols that are advantageously suitable for formulating a composition according to the present invention are those especially containing from 4 to 32 carbon atoms and preferably 4 to 12 carbon atoms.

According to one particular mode of the invention, the polyol is a compound of linear, branched or cyclic, saturated or unsaturated alkyl type, bearing on the alkyl chain at least four —OH functions.

According to another embodiment, a polyol that is suitable for use in the invention may be advantageously chosen from polyethylene glycols.

According to one embodiment, a composition of the invention may comprise a mixture of polyols.

Advantageously, the polyol may be chosen, for example, from ethylene glycol, pentaerythritol, trimethylolpropane, propylene glycol, 1,3 propanediol, butylene glycol, isoprene glycol, pentylene glycol, hexylene glycol, glycerol, polyglycerols such as glycerol oligomers, for instance diglycerol, erythritol, arabitol, adonitol, sorbitol, mannitol, xylitol, maltitol, lactitol, volemitol, dulcitol, glucose, fructose, xylose, trehalose, sucrose, maltose, saccharose and lactose, and mixtures thereof.

According to one preferred embodiment of the invention, the said polyol is chosen from ethylene glycol, pentaerythritol, trimethylolpropane, propylene glycol, polyglycerols, erythritol, sorbitol, mannitol, xylitol, maltitol, lactitol and volemitol, and mixtures thereof.

According to one embodiment, a mixture of polyol(s) that is suitable for use in the invention may advantageously comprise at least one compound of linear, branched or cyclic, saturated or unsaturated alkyl type, bearing on the alkyl chain at least four —OH functions, and preferably at least sorbitol.

A polyol that is suitable for use in the invention may advantageously be natural or of natural origin.

For the purposes of the present invention, the term "polyoxyethylenated ethers" means any compound derived from the addition of alkene oxides to a sugar.

The polyoxyethylenated ethers in accordance with the invention may be chosen from polyethylene oxide or polyethylene glycol (PEG), polypropylene glycol (PPG) and polytetramethylene glycol (PTMG), and mixtures thereof.

According to one particularly preferred mode of the invention, the hydrophilic binder is a polyol.

Advantageously, a hydrophilic binder in accordance with the invention is sorbitol.

IV—Dispersant

A dispersant that is suitable for use in the invention protects the various ingredients of the colouring particles that are solid at room temperature and atmospheric pressure against their aggregation or flocculation when it is placed in contact with an aqueous composition.

The dispersant according to the invention is different from the abovementioned hydrophilic binder.

A dispersant may be a surfactant, an oligomer, a polymer or a mixture of several thereof, bearing one or more functionalities that have strong affinity for the surface of the compounds to be dispersed.

In particular, they may be physically adsorbed onto the surface of the particles to be dispersed.

The colouring particles that are solid at room temperature and atmospheric pressure in accordance with the invention may comprise from 0.1% to 20% by weight, preferably from 0.5% to 10% by weight and better still from 1% to 7% by weight, or even from 2% to 5% by weight of dispersant(s), relative to the total weight of the said particles.

According to one particular embodiment, a dispersant in accordance with the invention is a surfactant.

As dispersants that are suitable for use in the invention, mention may be made especially of surfactants with high hydrophilicity, with an HLB of greater than 10, preferably greater than 13 and more particularly greater than 15.

The term "HLB of greater than or equal to 10" means a surfactant having, at 25° C., an HLB balance (hydrophilic-lipophilic balance), within the Griffin meaning, of greater than or equal to 10.

The HLB value according to Griffin is defined in J. Soc. Cosm. Chem. 1954 (volume 5), pages 249-256.

Reference may also be made to Kirk-Othmer's *Encyclopedia of Chemical Technology*, volume 22, pp. 333-432, 3rd edition, 1979, Wiley, for the definition of the (emulsifying) properties and functions of surfactants, in particular pp. 347-377 of this reference, for anionic and nonionic surfactants.

Reference may also be made to surfactants with an HLB of greater than or equal to 10 that are cited in McCutcheons Emulsifiers & Detergents, International edition of 1998 et seq. Examples that may be mentioned are those given on pages 223 to 231 of the HLB Index section of the 1998 edition.

A surfactant that is suitable for use in the invention may be chosen from ionic, anionic, cationic and nonionic surfactants, and mixtures thereof. The surfactant is preferably nonionic.

The nonionic dispersant may be chosen from polyoxyethylene glycol ethers or esters (POE/PEG ethers or esters) or polyoxypropylene glycol ethers or esters (PPG ethers or esters), from sugar ethers or esters, from glycerol or polyglycerol ethers or esters and from ethoxylated glyceride esters (POE glyceryl esters) or from mixtures thereof.

The POE ethers according to the invention may be, for example, PEG-40 hydrogenated castor oil, PEG-60 hydrogenated castor oil, PEG-40 stearate, jojoba wax PEG-120 ester, PEG-100 stearate or PEG-100 isostearate.

The sugar esters according to the invention may be, for example, sucrose laurate, sucrose palmitate, sucrose myristate, sucrose stearate or lauryl glucoside.

The ethoxylenated glycerides according to the invention may be chosen from PEG-80 glyceryl soyate, PEG-20 glyceryl stearate, PEG-60 almond glycerides, PEG-42 babassu glycerides, PEG-60 evening primrose glycerides, PEG-60 corn glycerides, PEG-45 palm kernel glycerides, PEG-60 maracuja glycerides or PEG-192 apricot kernel glycerides.

The nonionic dispersant is preferably a polyoxyethylenated ether, preferably with an HLB of greater than 15. This POE ether may be chosen, for example, from ceteareth-20, steareth-20, oleth-20, beheneth-25, steareth-21, ceteareth-25 and the oxyethylenated ether of cetearyl alcohol containing 25 oxyethylene groups, C12-13 pareth-23, oleth-30, laureth-23 or ceteareth-30.

The anionic dispersant may be chosen from sulfuric acid esters (sodium lauryl sulfate, sodium cetearyl sulfate), phosphoric acid esters (laureth-4 phosphate) and sarcosine derivatives (lauroyl sarcosine).

Advantageously, a dispersant in accordance with the invention is a nonionic surfactant.

Even more advantageously, a dispersant in accordance with the invention is an oxyethylenated cetylstearyl alcohol, preferably of ceteareth-25 type.

V—Non-Aqueous Binder

Advantageously, a non-aqueous binder in accordance with the invention may be chosen from oils, especially volatile and non-volatile oils of hydrocarbon-based, silicone or fluoro type, as described below, or from polyols as described previously.

B—Protocol for Preparing Colouring Particles

The various compounds constituting the colouring particles that are solid at room temperature and atmospheric pressure of the invention are dry-mixed, in proportions in accordance with the invention.

However, the effervescent system will have been prepared beforehand by mixing the acid and the base, especially citric acid and sodium (bi)carbonate, both in crystalline form, in the stoichiometric proportions of the effervescent reaction between the two constituents.

The anhydrous mixture of the said compounds obtained is heated on a water bath, at a temperature that especially makes it possible to reach the melting point of the hydrophilic binder, until the said binder is completely liquid. The binder will thus be chosen as a function of its solubility (as high as possible in water) but also as a function of its melting point, preferably less than 120° C., and even more preferentially less than 100° C.

The mixture is then cooled so as to ensure its precipitation in the form of solid colouring particles, which are collected and maintained under moderate stirring until completely cooled, so as to prevent them from aggregating into blocks.

The solid colouring particles are screened by screening through a screen with a mesh size, for example, of 1 mm or even less than 1 mm, and more particularly of between 50 μm and 5 mm. The colouring particles may especially have a size of between 50 μm and 5 mm, or even between 50 μm and 2 mm, or finally between 50 μm and 500 μm.

In particular, the manufacturing process may include the following steps:
- preparation of the effervescent system, for example by mixing citric acid and sodium (bi)carbonate in crystalline form, in stoichiometric properties,
- dry mixing of the pigments with the effervescent system, and a dispersant chosen, for example, from polyoxyethylenated ethers such as ceteareth-25, and a polyol such as sorbitol,
- heating the mixture to a temperature of about 100° C., to melt the polyol such as sorbitol, and then
- cooling the whole and subjecting it to moderate stirring until completely cooled to prevent aggregation into blocks,
- screening the particles obtained to the desired particle size.

As indicated previously, the said first composition may be either formed solely from or essentially from, or else formed partly from the said solid colouring particles and may then be, in the case of this latter alternative, in the form of a first "simplex" or "complex" composition as described previously.

In the latter alternative, the protocol for preparing such compositions differs from that described above only by the addition, after obtaining the colouring particles, of coloured and/or uncoloured pulverant material(s), optionally of the non-aqueous binder(s) and of the additional ingredient(s) defined previously, according to the standard protocols for formulating cosmetic compositions.

C—Various Forms of First Composition

C-1 Composition Formed Solely or Essentially from Colouring Particles in Accordance with the Invention.

A first composition may be formed solely or essentially from colouring particles that are solid at room temperature and atmospheric pressure formed from at least one hydrophilic dyestuff in a content of greater than 60% by weight, of at least one effervescent system in a content of less than 20% by weight, relative to the total weight of the said colouring particles, of at least one hydrophilic binder and of at least one dispersant that is different from the said hydrophilic binder.

More particularly, the dyestuff is advantageously between 75% and 85% by weight, the effervescent system is advantageously between 5% and 15% by weight, the hydrophilic binder is advantageously between 5% and 8% by weight and the dispersant is advantageously between 2% and 5% by weight, relative to the total weight of the said colouring particles.

Thus, advantageously, an anhydrous cosmetic composition of this type is formed totally or partly of colouring particles that are solid at room temperature and atmospheric pressure formed from 80% by weight of hydrophilic dyestuff(s), 10% by weight of effervescent system(s), 6% to 7% by weight of hydrophilic binder(s) and 3% to 4% by weight of dispersant(s), relative to the total weight of the said first composition.

The said composition may also comprise a non-aqueous binder, as described previously.

C-2 Composition Formed Only Partly from Colouring Particles in Accordance With the Invention.

A first such composition formed only partly from colouring particles in accordance with the invention, i.e. which may also comprise at least one coloured and/or uncoloured pulverant material and optionally at least one non-aqueous binder, may be, for example, an anhydrous solid composition such as a foundation, eye shadow, face powder or blusher composition, especially in compact or loose form. In particular, the said composition will comprise at least one coloured and/or uncoloured pulverant material, chosen especially from pigments, nacres and fillers, and mixtures thereof.

In particular, they will be fillers.

For the purposes of the invention, the term "fillers" should be understood as meaning colourless or white solid particles of any form, which are in an insoluble and dispersed form in the medium of the composition. These fillers, of mineral or organic, natural or synthetic nature, give the composition softness and give the makeup result a matt effect and uniformity.

The fillers may be mineral or organic, of any form, platelet-shaped, spherical or oblong, irrespective of the crystallographic form (for example lamellar, cubic, hexagonal, orthorhombic, etc.). Mention may be made of talc, mica, silica, kaolin, polyamide powder)(Nylon®, poly-β-alanine powder and polyethylene powder, powders of tetrafluoroethylene polymers)(Téflon®, lauroyllysine, starch, boron nitride, bismuth oxychloride, hollow polymer microspheres such as those of polyvinylidene chloride/acrylonitrile, for instance Expancel® (Nobel Industrie), acrylic acid copolymer microspheres, silicone resin microbeads (for example Tospearls® from Toshiba), elastomeric polyorganosiloxane particles, precipitated calcium carbonate, magnesium carbonate, magnesium hydrogen carbonate, hydroxyapatite, barium sulfate, aluminium oxides, polyurethane powders, colouring fillers, hollow silica microspheres, glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate, and mixtures thereof.

Advantageously, a first anhydrous composition of this type, and in particular a "simplex" composition, may comprise from 10% to 70% by weight, preferably from 20% to 60% by weight and better still from 30% to 50% by weight of filler(s) relative to the total weight of the said composition.

A first "complex" composition, as described previously, will comprise, besides the non-aqueous binder and the coloured and/or uncoloured pulverant materials, at least one additional ingredient chosen from surfactants, gelling agents, optionally polymers, fibres, chelating agents, active agents and fragrances, and mixtures thereof. Examples of such additional ingredients are described below.

The first composition according to the invention may be in a solid to pasty form or in a fluid form. Advantageously, it will be in a solid to pasty form.

C—Second Composition

As stated previously, for the purposes of the invention, a "second composition" is a composition comprising at least one aqueous phase.

The said aqueous phase may be free or trapped, on or in particles. The second composition may thus be in a fluid, gelled or pulverant form. In the latter case, the aqueous phase adsorbed onto solid particles may then be released by mechanical shear in the course of mixing with the first composition.

The placing in contact of the first composition with this second composition comprising at least one aqueous phase causes spontaneous dispersion of the solid colouring particles comprising the hydrophilic dyestuff(s).

The aqueous phase of this second composition comprises water and, where appropriate, at least one water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the compositions according to the invention may also be volatile.

Among the water-soluble solvents that may be used in the second composition in accordance with the invention, mention may be made especially of lower monoalcohols containing from 1 to 5 carbon atoms such as ethanol and isopropanol, glycols containing from 2 to 8 carbon atoms such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in the second composition in a content ranging from 10% to 100% by weight and preferably ranging from 20% to 80% by weight relative to the total weight of the composition.

According to one particular embodiment, and especially when the first composition is formed solely or essentially from colouring particles according to the invention, the second composition of the invention is a cosmetic composition comprising at least one aqueous phase that is compatible with the first anhydrous composition of the invention, in particular a composition for caring for, for the hygiene of and/or for making up a keratin material.

Still according to this embodiment, the second composition may be in the form of an emulsion.

The second composition according to the invention may in particular be in the form of an emulsion obtained by dispersing an aqueous phase in a fatty phase (W/O) or a fatty phase in an aqueous phase (O/W), of liquid or semi-liquid consistency of the milk type, or of soft, semi-solid or solid consistency of the cream or gel type, or alternatively a multiple emulsion (W/O/W or O/W/0).

These compositions are prepared according to the usual methods.

According to one particular variant of this embodiment, the second composition is an 0/W emulsion, which may be, for example, in the form of a care cream.

Advantageously, the second composition has a viscosity at 20° C. greater than or equal to 15 000 cP.

The second composition according to the invention can also comprise at least one surfactant.

The surfactant can be chosen from amphoteric, anionic, cationic or nonionic surface-active agents, preferably nonionic surface-active agents.

When a product according to the invention is intended to the care and/or makeup for the skin and/or lips, nonionic or anionic surface-active agents are preferred, in particular nonionic surface-active agents.

When a product according to the invention is a hair product, cationic surface-active agents are preferred.

Mention may in particular be made, alone or as mixtures, of:

a) nonionic surface-active agents with an HLB of less than 8 at 25° C., optionally in combination with one or more nonionic surface-active agents with an HLB of greater than 8 at 25° C., such as mentioned below, for example:
  monosaccharide esters and ethers, such as sucrose stearates, sucrose cocoate, sorbitan stearate and their mixtures;
  esters of fatty acids, in particular C8-C24 and, preferably, C16-C22 fatty acids, and of polyols, in particular of glycerol or of sorbitol, such as glyceryl stearate, glyceryl laurate, polyglyceryl-2 stearate, sorbitan tristearate and glyceryl ricinoleate;
  lecithins, such as soya bean lecithins;
  oxyethylenated and/or oxypropylenated ethers (which can comprise from 1 to 150 ethylene oxide and/or propylene oxide groups) of fatty alcohols (in particular of C8-C24 and, preferably, C12-C18 alcohols), such as the oxyethylenated ether of stearyl alcohol comprising 2 ethylene oxide units (CTFA name: Steareth-2);
  silicone surfactants, such as dimethicone copolyols and alkyl dimethicone copolyols, for example the cyclomethicone/dimethicone copolyol mixture sold under the name Q2-3225C® by Dow Corning;

b) nonionic surface-active agents with an HLB of greater than or equal to 8 at 25° C., for example:
  monosaccharide esters and ethers, such as the mixture of cetearyl glucoside and of cetyl and stearyl alcohols, for example Montanov 68 from Seppic;
  oxyethylenated and/or oxypropylenated glycerol ethers which can comprise from 1 to 150 ethylene oxide and/or propylene oxide units;
  oxyethylenated and/or oxypropylenated ethers (which can comprise from 1 to 150 ethylene oxide and/or propylene oxide units) of fatty alcohols, in particular C8-C24 and, preferably, C12-C18 fatty alcohols, such as the oxyethylenated ether of stearyl alcohol comprising 20 ethylene oxide units (CTFA name: Steareth-20), the oxyethylenated ether of cetearyl alcohol comprising 30 ethylene oxide units (Ceteareth-30) and the oxyethylenated ether of the mixture of C12-C15 fatty alcohols comprising 7 ethylene oxide units (C12-15 Pareth-7);
  esters of fatty acids, in particular $C_8$-$C_{24}$ and, preferably, C16-C22 fatty acids, and of polyethylene glycol (or PEG) (which can comprise from 1 to 150 ethylene oxide units), such as PEG-50 stearate and PEG-40 monostearate;
  esters of fatty acids, in particular C8-C24 and, preferably, C16-C22 fatty acids, and of oxyethylenated and/or oxypropylenated glycerol ethers (which can comprise from 1 to 150 ethylene oxide and/or propylene oxide units), such as polyoxyethylenated glyceryl monostearate comprising 200 ethylene oxide units, polyoxyethylenated glyceryl stearate comprising 30 ethylene oxide units, polyoxyethylenated glyceryl oleate comprising 30 ethylene oxide units, polyoxyethylenated glyceryl cocoate comprising 30 ethylene oxide units, polyoxyethylenated glyceryl isostearate comprising 30 ethylene oxide units and polyoxyethylenated glyceryl laurate comprising 30 ethylene oxide units; esters of fatty acids, in particular C8-C24 and, preferably, C16-C22 fatty acids, and of oxyethylenated and/or oxypropylenated sorbitol ethers (which can comprise from 1 to 150 ethylene oxide and/or propylene oxide units), such as polysorbate 20 and polysorbate 60;
  dimethicone copolyol, such as Q2-5220® from Dow Corning;
  dimethicone copolyol benzoate, such as Finsolv SLB 101® and 201® from Finetex;
  propylene oxide and ethylene oxide copolymers, also known as EO/PO polycondensates, which are copolymers composed of polyethylene glycol and polypropylene glycol blocks, such as, for example, polyethylene glycol/polypropylene glycol/polyethylene glycol triblock polycondensates;

c) anionic surfactants, such as:
salts of C16-C30 fatty acids, in particular amine salts, such as triethanolamine stearate or 2-amino-2-methylpropane-1,3-diol stearate;
salts of polyoxyethylenated fatty acids, in particular amine salts or alkali metal salts, and their mixtures;
phosphoric esters and their salts, such as "DEA oleth-10 phosphate" (Crodafos N 10N from Croda) or monopotassium monocetyl phosphate;
sulphosuccinates, such as "Disodium PEG-5 citrate lauryl sulfosuccinate" and "Disodium ricinoleamido MEA sulfosuccinate";
alkyl ether sulphates, such as sodium lauryl ether sulphate;
isethionates;
acylglutamates, such as "Disodium hydrogenated tallow glutamate" (Amisoft HS-21 R® from Ajinomoto) and sodium stearoyl glutamate (Amisoft HS-11 PF® from Ajinomoto);
soya bean derivatives, such as potassium soyate;
citrates, such as glyceryl stearate citrate;
proline derivatives, such as sodium palmitoyl proline or the mixture of sodium palmitoyl sarcosinate, magnesium palmitoyl glutamate, palmitic acid and palmitoyl proline (Sepifeel One from Seppic);
lactylates, such as sodium stearoyl lactylate;

sarcosinates, such as sodium palmitoyl sarcosinate or the 75/25 mixture of stearoyl sarcosine and myristoyl sarcosine;
sulphonates, such as sodium C14-17 sec alkyl sulphonate;
glycinates, such as sodium cocoyl glycinate;
d) cationic surfactants, such as:
alkylimidazolidiniums, such as isostearyl ethylimidonium ethosulphate;
ammonium salts, such as (C12-30 alkyl)tri(C1-4 alkyl) ammonium halides, such as N,N,N-trimethyl-1-docosanaminium chloride (or behentrimonium chloride);
e) amphoteric surfactants, such as N-acylamino acids, for example N-alkylaminoacetates and disodium cocoamphodiacetate, and amine oxides, such as stearamine oxide.

According to one particular mode of the invention, the second composition comprises at least one nonionic surfactant. The said nonionic surfactant may be a nonionic silicone surfactant or a hydrocarbon-based nonionic surfactant. Advantageously, a hydrocarbon-based nonionic surfactant will be used in the case of an O/W emulsion.

Nonionic Silicone Surfactant

The nonionic silicone surfactant is preferably chosen from polydimethyl (or dialkyl) silicones containing polyoxyalkylenated (polyoxyethylenated (or POE) and/or polyoxypropylenated (or PPO)) hydrophilic side and/or end groups, polydialkyl silicones containing polyglycerolated or glycerolated side and/or end groups, and a mixture thereof.

The nonionic silicone surfactant may be chosen in particular from:
a C8-C22 alkyl dimethicone copolyol, i.e. an oxypropylenated and/or oxyethylenated polymethyl(C8-C22) alkyldimethylmethylsiloxane.

The C8-C22 alkyl dimethicone copolyol is advantageously a compound of formula (I) below:

$$(CH_3)_3Si-O-\left[\begin{array}{c}CH_3\\|\\Si-O\\|\\(CH_2)_p\\|\\CH_3\end{array}\right]_o\left[\begin{array}{c}CH_3\\|\\Si-O\\|\\(CH_2)_q\\|\\O\\|\\PE\end{array}\right]_m\left[\begin{array}{c}CH_3\\|\\Si-O\\|\\CH_3\end{array}\right]_n Si(CH_3)_3 \quad (I)$$

in which:
PE represents $(-C_2H_4O)x-(C_3H_6O)y-R$, R being chosen from a hydrogen atom and an alkyl radical of 1 to 4 carbon atoms, x ranging from 0 to 100 and y ranging from 0 to 80, x and y not simultaneously being 0
m ranging from 1 to 40
n ranging from 10 to 200
o ranging from 1 to 100
p ranging from 7 to 21
q ranging from 0 to 4
and preferably:
R=H
m=1 to 10
n=10 to 100
o=1 to 30
p=15
q=3

A $C_8$-$C_{22}$ alkyl dimethicone copolyol that may be mentioned is cetyldimethicone copolyol, for instance the product sold under the name Abil EM-90 by the company Goldschmidt.

a dimethicone copolyol, i.e. an oxypropylenated and/or oxyethylenated polydimethylmethylsiloxane. It does not contain any long-chain alkyl groups of more than 8 carbon atoms, especially $C_8$-$C_{22}$.

Dimethicone copolyols that may be used are those corresponding to formula (II) below:

$$R_1-Si-O-\left[\begin{array}{c}CH_3\\|\\SiO\\|\\CH_3\end{array}\right]_A\left[\begin{array}{c}CH_3\\|\\SiO\\|\\R_2\end{array}\right]_B\begin{array}{c}CH_3\\|\\Si-R_3\\|\\CH_3\end{array} \quad (II)$$

in which:
$R_1$, $R_2$ and $R_3$, independently of each other, represent a $C_1$-$C_6$ alkyl radical or a radical $-(CH_2)x-(OCH_2CH_2)y-(OCH_2CH_2)z-OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;
A is an integer ranging from 0 to 200;
B is an integer ranging from 0 to 50; on condition that A and B are not simultaneously equal to zero;
x is an integer ranging from 1 to 6;
y is an integer ranging from 1 to 30;
z is an integer ranging from 0 to 5.

According to one preferred embodiment of the invention, in the compound of formula (II), $R_1=R_3=$methyl radical, x is an integer ranging from 2 to 6 and y is an integer ranging from 4 to 30. $R_4$ is in particular a hydrogen.

As examples of compounds of formula (II), mention may be made of the compounds of formula (III):

$$(CH_3)_3SiO-[(CH_3)_2SiO]A-(CH_3SiO)B-Si(CH_3)_3 \quad (III)$$
$$|$$
$$(CH_2)_2-(OCH_2CH_2)y-OH$$

in which A is an integer ranging from 20 to 105, B is an integer ranging from 2 to 10 and y is an integer ranging from 10 to 20.

As examples of silicone compounds of formula (II), mention may also be made of the compounds of formula (IV):

$$HO-(CH_2CH_2O)y-(CH_2)_3-[(CH_3)_2SiO]A'-[(CH_3)_2Si]-(CH_2)_3-(OCH_2CH_2)y-OH \quad (IV)$$

in which A' and y are integers ranging from 10 to 20.

Dimethicone copolyols that may be used include those sold under the names DC 5329, DC 7439-146, DC2-5695 and Q4-3667 by the company Dow Corning; KF-6013, KF-6015, KF-6016 and KF-6017 by the company Shin-Etsu.

The compounds DC 5329, DC 7439-146 and DC2-5695 are compounds of formula (III) in which, respectively, A is 22, B is 2 and y is 12; A is 103, B is 10 and y is 12; A is 27, B is 3 and y is 12.

The nonionic silicone surfactant is preferably chosen from:
I—polydimethyl (or dialkyl) silicones containing polyoxyalkylenated polyoxyethylenated (or POE) and/or polyoxypropylenated (or POP) hydrophilic side and/or end groups. Furthermore, these silicone surfactants preferably comprise alkyl side groups that are more hydrophobic than the previously mentioned linear or branched $C_1$ to $C_{20}$ and preferably $C_4$ to $C_{20}$ side and/or end groups, preferably linear alkyl groups, such as lauryl or cetyl. These surfactants may also bear organosiloxane side groups.

In particular, in this first category, mention may be made of:
polydimethylsiloxanes containing POE side and/or end groups, especially such as KF-6011, KF-6012, KF-6013, KF-6015, KF-6016 and KF-6017 from the company Shin-Etsu or bis-PEG/PPG-14/14 dimethicone & cyclopentasiloxane sold under the name Abil EM 97 by the company Evonik Goldschmidt;
polydimethylsiloxanes containing POE side groups and alkyl side groups, especially such as cetyl PEG-PPG 10/1 and dimethicone, sold under the name Abil EM 90 by the company Evonik Goldschmidt;
branched polydimethylsiloxanes containing POE side groups, especially such as PEG-9 polydimethyl siloxyethyl dimethicone, sold under the name KF-6028 by the company Shin-Etsu;
branched polydimethylsiloxanes containing alkyl side groups, especially such as lauryl PEG-9 polydimethyl siloxyethyl dimethicone, sold under the name KF-6038 by the company Shin-Etsu.

II—polydialkyl silicones containing polyglycerol or glycerol side and/or end groups. These silicone surfactants also preferably comprise linear or branched $C_1$ to $C_{20}$ alkyl side groups, and preferably also linear alkyl groups such as lauryl or cetyl. Similarly, these silicone and glycerolated surfactants may also bear organosiloxane side groups.

In particular, mention may be made in this category of:
polydimethylsiloxanes containing polyglycerol side groups, such as polyglyceryl-3 disiloxane dimethicone, sold under the name KF-6100 by the company Shin-Etsu;
branched polydimethylsiloxanes containing polyglycerol side groups, such as polyglyceryl-3 polydimethyl siloxyethyl dimethicone, sold under the name KF-6104 by the company Shin-Etsu;
branched polydimethylsiloxanes containing polyglycerol side groups and alkyl side groups, such as lauryl polyglyceryl-3 polydimethyl siloxyethyl dimethicone, sold under the name KF-6105 by the company Shin-Etsu.

Among the nonionic silicone surfactants, cetyl PEG/PPG-10/1 dimethicone sold under the name Abil EM 90 by the company Evonik Goldschmidt is preferred.

According to another embodiment, bis-paying/PPG-14/14 dimethicone & cyclopentasiloxane sold under the name Abil EM 97 by the company Evonik Goldschmidt is used as nonionic silicone surfactant.

It is also possible to use a mixture of these two preferred nonionic silicone surfactants.

The nonionic silicone surfactant may be present in the second composition according to the invention in a content ranging from 0.1% to 10% by weight, preferably ranging from 0.5% to 8% by weight and preferentially ranging from 0.5% to 7% by weight, relative to the total weight of the composition.

Nonionic Hydrocarbon-Based Surfactant

Among the nonionic hydrocarbon-based surfactants, mention may be made especially of:
fatty alcohols;
polyol esters of a fatty acid containing a saturated or unsaturated chain comprising, for example, from 8 to 24 carbon atoms and better still from 12 to 22 carbon atoms, and oxyalkylenated derivatives thereof, i.e. derivatives comprising oxyethylene and/or oxypropylene units, such as glyceryl esters of $C_8$-$C_{24}$ fatty acids, and oxyalkylenated derivatives thereof;
polyethylene glycol esters of $C_8$-$C_{24}$ fatty acids, and oxyalkylenated derivatives thereof;
sorbitol esters of $C_8$-$C_{24}$ fatty acids, and oxyalkylenated derivatives thereof;
sugar (sucrose, glucose or alkylglucose) esters of $C_8$-$C_{24}$ fatty acids, and oxyalkylenated derivatives thereof;
fatty alkyl ethers;
sugar ethers of $C_8$-$C_{24}$ fatty alcohols, and mixtures thereof.

Fatty alcohols that may especially be mentioned include cetyl alcohol, stearyl alcohol, behenyl alcohol and myristyl alcohol, and mixtures thereof.

Glyceryl esters of fatty acids that may especially be mentioned include glyceryl stearate (glyceryl mono-, di- and/or tristearate) (CTFA name: glyceryl stearate) or glyceryl ricinoleate, and mixtures thereof. Mention may also be made of polyglycerolated fatty acid esters comprising at least 3 glycerol ether units, such as polyglyceryl-3; and in particular polyglyceryl-4 isostearate sold under the name Isolan GI 34® by the company Evonik Goldschmidt.

Polyethylene glycol esters of fatty acids that may especially be mentioned include polyethylene glycol stearate (polyethylene glycol mono-, di- and/or tristearate) and more especially polyethylene glycol 500E monostearate (CTFA name: PEG-50 stearate) and polyethylene glycol 1000E monostearate (CTFA name: PEG-100 stearate), and mixtures thereof.

Mixtures of these surfactants may also be used, for instance the product containing glyceryl stearate and PEG-100 stearate, sold under the name Arlacel 165 by the company Croda, and the product containing glyceryl stearate (glyceryl monodistearate) and potassium stearate, sold under the name Tegin by the company Goldschmidt (CTFA name: glyceryl stearate SE).

Fatty acid esters of glucose or of alkylglucose that may be mentioned in particular include glucose palmitate, alkylglucose sesquistearates, for instance methylglucose sesquistearate, alkylglucose palmitates, for instance methylglucose palmitate or ethylglucose palmitate, fatty esters of methylglucoside and more especially the diester of methylglucoside and of oleic acid (CTFA name: Methyl glucose dioleate); the mixed ester of methylglucoside and of the oleic acid/hydroxystearic acid mixture (CTFA name: Methyl glucose dioleate/hydroxysterate); the ester of methylglucoside and of isostearic acid (CTFA name: Methyl glucose isostearate); the ester of methylglucoside and of lauric acid (CTFA name: Methyl glucose laurate); the mixture of the monoester and diester of methylglucoside and of isostearic acid (CTFA name: Methyl glucose sesquiisostearate); the mixture of the monoester and diester of methylglucoside and of stearic acid (CTFA name: Methyl glucose sesquistearate) and in particular the product sold under the name Glucate SS by the company Amerchol, and mixtures thereof.

Examples of oxyethylenated ethers of a fatty acid and of glucose or of alkylglucose that may be mentioned include the oxyethylenated ethers of a fatty acid and of methylglucose, and in particular the polyethylene glycol ether of the diester of methyl glucose and of stearic acid containing about 20 mol of ethylene oxide (CTFA name: PEG-20 methyl glucose distearate), such as the product sold under the name Glucam E-20 distearate by the company Amerchol; the polyethylene glycol ether of the mixture of monoester and diester of methylglucose and of stearic acid containing about 20 mol of ethylene oxide (CTFA name: PEG-20 methyl glucose sesquistearate) and in particular the product sold under the name Glucamate SSE-20 by the company Amerchol, and the product sold under the name Grillocose PSE-20 by the company Goldschmidt, and mixtures thereof.

Examples of sucrose esters that may be mentioned include sucrose palmitostearate, sucrose stearate and sucrose monolaurate.

Examples of fatty alkyl ethers that may be mentioned include polyethylene glycol ethers of fatty alcohols containing from 8 to 30 carbon atoms and especially from 10 to 22 carbon atoms, such as polyethylene glycol ethers of cetyl alcohol, of stearyl alcohol or of cetearyl alcohol (mixture of cetyl alcohol and stearyl alcohol). Examples that may be mentioned include ethers comprising from 1 to 200 and preferably from 2 to 100 oxyethylene groups, such as those of CTFA name Ceteareth-20 and Ceteareth-30, and mixtures thereof. Mention may also be made of fatty alkyl ethers of polyglycerols with at least 3 glyceryl ether units; fatty alkyl ethers of polyoxyalkylenes (POE and/or POE/POP) with at least 3 POE groups.

Sugar ethers that may especially be mentioned are alkylpolyglucosides, for example decylglucoside, for instance the product sold under the name Mydol 10 by the company Kao Chemicals, the product sold under the name Plantaren 2000 by the company Henkel, and the product sold under the name Oramix NS10 by the company SEPPIC; caprylyl/capryl glucoside, for instance the product sold under the name Oramix CG 110 by the company SEPPIC or under the name Lutensol GD 70 by the company BASF; laurylglucoside, for instance the products sold under the names Plantaren 1200 N and Plantacare 1200 by the company Henkel; cocoglucoside, for instance the product sold under the name Plantacare 818/UP by the company Henkel; cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel; arachidyl glucoside, for example in the form of the mixture of arachidyl alcohol and behenyl alcohol and arachidyl glucoside, sold under the name Montanov 202 by the company SEPPIC; cocoylethylglucoside, for example in the form of the mixture (35/65) with cetyl alcohol and stearyl alcohol, sold under the name Montanov 82 by the company SEPPIC; and mixtures thereof.

The nonionic hydrocarbon-based surfactant may be present in the second composition according to the invention in a content ranging from 0.1% to 10% by weight, preferably ranging from 0.5% to 8% by weight and preferentially ranging from 0.5% to 7% by weight, relative to the total weight of the composition.

According to another particular embodiment, when the first composition is in a "complex" form, the second composition may in particular comprise more than 80% by weight, preferably more than 85% by weight and better still more than 90% by weight of water relative to its total weight.

Such a composition may especially take the form of an aqueous solution, lotion or gel.

According to one variant of this embodiment, the second composition of the invention is water.

The second composition may also comprise one or more gelling agents, which are especially hydrophilic, i.e. they are soluble or dispersible in water.

Hydrophilic gelling agents that may be mentioned in particular include water-soluble or water-dispersible thickening polymers. These polymers may be chosen especially from: modified or unmodified carboxyvinyl polymers, such as the products sold under the names Carbopol (CTFA name: carbomer) by the company Goodrich; polyacrylates and polymethacrylates such as the products sold under the names Lubrajel and Norgel by the company Guardian or under the name Hispagel by the company Hispano Chimica; polyacrylamides; optionally crosslinked and/or neutralized 2-acrylamido-2-methylpropane sulfonic acid polymers and copolymers, for instance the poly(2-acrylamido-2-methylpropanesulfonic acid) sold by the company Clariant under the name "Hostacerin AMPS" (CTFA name: ammonium polyacryldimethyltauramide); crosslinked anionic copolymers of acrylamide and of AMPS, which are in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellulo se and hydroxypropylcellulose; sodium hyaluronate; and mixtures thereof.

According to a preferred mode, the second composition comprises at least one hydrophilic gelling agent chosen among polysaccharide biopolymers, for instance xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellulo se and hydroxypropylcellulose; sodium hyaluronate; and mixtures thereof.

According to a more particular preferred mode, the second composition comprises at least xanthan gum as hydrophilic gelling agent.

According to a more particular preferred mode, the second composition comprises at least sodium hyluronate as hydrophilic gelling agent.

According to a particular mode, the second composition of the invention is an aqueous gel, in particular a gel of modified or non modified carboxyvinyl polymers such as the product sold under the name Carbopol (CTFA name: carbomer) by the company Goodrich.

Such gel is generally known to be slightly compatible with classic pigments. A first composition according to the invention presents the advantage to allow to homogeneously pigment this second composition.

Examples of lipophilic gelling agents that may be mentioned include modified clays such as modified magnesium silicate (Bentone Gel VS38 from Rheox), or hectorite modified with distearyldimethylammonium chloride (CTFA name: Disteardimonium hectorite) sold under the name Bentone 38 CE by the company Rheox.

The second composition may also comprise at least one cosmetic active agent.

The compositions of this type may be in the form of a face, lips and/or body care or makeup product, and may be conditioned, for example, in the form of cream in a jar or of fluid in a tube or a pump-dispensing bottle.

Other Components that May be Contained in the First and/or Second Compositions

Physiologically Acceptable Medium

A composition of the invention may also comprise a physiologically acceptable medium.

The term "physiologically acceptable medium" is intended to denote a medium that is particularly suitable for applying a product of the invention to keratin materials, especially the skin and more particularly to facial skin.

The physiologically acceptable medium is generally adapted to the nature of the support onto which the product is to be applied, and also to the aspect in which the solid anhydrous composition or the product is to be conditioned.

Liquid Fatty Phase

Either of the first and second compositions of the invention may also comprise at least one fatty phase that is liquid at room temperature and atmospheric pressure, and especially at least one oil as mentioned below.

The term "oil" means any fatty substance that is in liquid form at room temperature and atmospheric pressure.

An oily phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They may be of animal, plant, mineral or synthetic origin. According to one embodiment variant, oils of plant origin are preferred.

For the purposes of the present invention, the term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and at atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

For the purposes of the present invention, the term "non-volatile oil" means an oil with a vapour pressure of less than 0.13 Pa.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

Volatile Oils

The volatile oils may be chosen from hydrocarbon-based oils containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicones, especially those with a viscosity<8 centistokes (cSt) ($8 \times 10^{-6}$ m²/s) and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclo-hexasiloxane, heptamethylhexyltrisiloxane, heptamethyloctyltrisiloxane, hexamethyl-disiloxane, octamethyltrisiloxane, decamethyltetrasiloxane and dodecamethyl-pentasiloxane, and mixtures thereof.

Volatile fluoro oils may also be used, such as nonafluoromethoxybutane or perfluoromethylcyclopentane, and mixtures thereof.

Non-Volatile Oils

The non-volatile oils may be chosen especially from non-volatile hydrocarbon-based, fluoro and/or silicone oils.

Non-volatile hydrocarbon-based oils that may especially be mentioned include:

hydrocarbon-based oils of animal origin;

hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camellina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stearineries Dubois or those sold under the names Miglyo1810, 812® and 818® by the company Dynamit Nobel;

synthetic ethers containing from 10 to 40 carbon atoms, such as dicaprylyl ether;

synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2>10$. The esters may be chosen especially from fatty acid esters of alcohols, for instance: cetostearyl octanoate, isopropyl alcohol esters, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters such as isodecyl neopentanoate, isotridecyl neopentanoate, and isononanoic acid esters, for instance isononyl isononanoate and isotridecyl isononanoate, polyol esters and pentaerythritol esters, for instance dipentaerythrityl tetrahydroxystearate/tetraisostearate, fatty alcohols that are liquid at room temperature, with a branched and/or unsaturated carbon-based chain containing from 12 to 26 carbon atoms, for instance 2-octyldodecanol, isostearyl alcohol and oleyl alcohol;

$C_{12}$-$C_{22}$ higher fatty acids, such as oleic acid, linoleic acid or linolenic acid, and mixtures thereof;

dialkyl carbonates, the two alkyl chains possibly being identical or different, such as dicaprylyl carbonate sold under the name Cetiol CC® by Cognis; and oils of high molar mass, in particular with a molar mass ranging from about 400 to about 2000 g/mol and in particular from about 650 to about 1600 g/mol. As oils of high molar mass that may be used in the present invention, mention may be made especially of linear fatty acid esters with a total carbon number ranging from 35 to 70, for instance pentaerythrityl tetrapelargonate, hydroxylated esters, such as polyglyceryl-2 triisostearate, aromatic esters, such as tridecyl trimellitate, esters of branched $C_{24}$-$C_{28}$ fatty alcohols or fatty acids, such as those described in U.S. Pat. No. 6,491,927, and pentaerythritol esters, and especially triisoarachidyl citrate, glyceryl triisostearate, glyceryl tris(2-decyl)tetradecanoate, polyglyceryl-2 tetraisostearate or pentaerythrityl tetrakis(2-decyl)tetradecanoate; phenyl silicones, such as Belsil PDM 1000 from the company Wacker (MM=9000 g/mol), non-volatile polydimethylsiloxanes (PDMS), PDMSs comprising alkyl or alkoxy groups that are pendent and/or at the end of the silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, dimethicones or phenyl trimethicones with a viscosity of less than or equal to 100 cSt, and mixtures thereof; and also mixtures of these various oils.

Additive

Either of the first and second compositions of the invention may also comprise any additive usually used in the field concerned, chosen, for example, from pigments, nacres, fillers and surfactants, different from those mentioned previously, but also chosen from waxes, pasty compounds, gums, semi-crystalline polymers, plasticizers, gelling agents, thickeners, chelating agents, fibres, preserving agents, fragrances, neutralizers, UV stabilizers, and mixtures thereof.

It is a matter of routine operations for a person skilled in the art to adjust the nature and amount of the additives present in the compositions in accordance with the invention such that the desired cosmetic properties thereof are not thereby affected.

According to one embodiment, a product of the invention may advantageously be intended for forming a foundation.

Packaging Article

As indicated previously, one aim of the invention is to propose an easy means for giving a colour and for modifying and/or correcting the colour properties of a cosmetic composition.

Thus, a subject of the invention is also a packaging article comprising at least a first composition according to the invention, or even several first compositions.

For the purposes of an article, a first composition may be in various forms, for example in the form of a loose or compact powder.

According to a first variant, when the said first composition is a loose powder, the article may be in the form of a sachet, optionally water-soluble, which may, where appropriate, be immersed as such in an aqueous medium forming the composition to be dyed.

It may also be a capsule, a spoon, a salt cellar or a mill, the particles of which are released by the user.

According to a second variant, when the said first composition is a compacted or aggregated powder, it may be placed on the surface of an article intended to come into contact with the aqueous medium forming the composition to be coloured.

Thus, like a match, the first composition may be deposited onto one of the ends of an article in a longitudinal form of stick type. The placing in contact of the first composition is then performed by dipping at least the coated end of the first composition in the composition to be coloured.

If necessary, the dissolution of the first composition may be accelerated by manual stirring of this end in the composition to be coloured.

The article may also be in the form of a water-soluble nonwoven material, or water-soluble granules or beads intended to be introduced as such into the composition to be dyed.

For the sake of optimum storage, but also for ease of use, the articles defined above may be in the form of single doses, and may thus allow the user to perform extemporaneous mixing between the first composition and the composition to be dyed, especially the second composition, for example in the palm of the hand, or in the packaging article containing the composition to be dyed (jar, etc.), or directly onto the site of application or into or onto an associated support.

According to a particular mode, the extemporaneous mixing between the first composition and the composition to be dyed, especially the second composition, is not realized inside the packaging article comprising the composition to be dyed but rather in the palm of the hand.

The user may use one or more single doses of first composition, as a function of the desired colour effect.

According to another variant, said first composition, especially under loose powder form, may be glued on a water-insoluble solid support, for example a paper or a paperboard support, so that it is still possible to take the powder with an applicator, such as for example a brush or a finger, and to mix it with a small amount of the second composition.

The mixture thus obtained may or may not be intended for a single use, in which case the user is capable of subsequently correcting the colour properties of the said mixture.

The invention is illustrated in greater detail by the examples described below. Unless otherwise indicated, the amounts indicated are expressed as mass percentages.

EXAMPLE 1

Solid Anhydrous Compositions Formed Solely from Colouring Particles in Accordance with the Invention Composition A

| | Starting material | Weight % |
|---|---|---|
| | Pigment* | 80 |
| | Effervescent system | 10 |
| of which: | Citric acid | 6.5 |
| | Sodium carbonate | 3.5 |
| | Sorbitol | 6.7 |
| | Oxyethylenated (25 OE) cetylstearyl alcohol (Cremophor A 25, BASF) | 3.3 |

*Pigments = yellow iron oxide, brown iron oxide, red iron oxide, black iron oxide, titanium dioxide, taken alone or as a mixture.
Various compositions of type A that will be named P1 to P4 in the rest of the examples are prepared, with:
P1 = composition A with yellow iron oxide (Sunpuro Yellow Iron Oxide C33-9001, sold by the company Sun),
P2 = composition A with red iron oxide (Sunpuro Red Iron Oxide C33-8001, sold by the company Sun),
P3 = composition A with black iron oxide (Sunpuro Black Iron Oxide C33-7001, sold by the company Sun),
P4 = composition A with titanium dioxide (Hombitan FF Pharma, sold by the company Sachtleben).

Composition B

| | Starting material | Weight % |
|---|---|---|
| | Nacre (mica-titanium oxide: Timiron Super Red 117187) | 80 |
| | Effervescent system | 10 |
| of which: | Citric acid | 6.5 |
| | Sodium carbonate | 3.5 |
| | Xylitol | 6.5 |

-continued

| Starting material | Weight % |
|---|---|
| Oxyethylenated (25 OE) cetylstearyl alcohol (Cremophor A 25 ®, BASF) | 3.5 |

Each of the compositions A and B is obtained according to the protocol defined in the description.

It is found that such solid anhydrous compositions, formed solely from colouring particles in accordance with the invention, when they are mixed with a second composition comprising at least one aqueous phase, or even water in a concentration of 3% to 20% by weight and better still from 5% to 15% by weight relative to the total weight of the mixture obtained, disperse spontaneously therein at room temperature while ensuring immediate and optimum colour development of the said second composition.

EXAMPLE 2

Comparative Example with Respect to the Content of Dispersant

Four compositions a, b, c and d formed solely from colouring particles in accordance with the invention and as defined in the table below are prepared according to the protocol defined in the description.

|   | Red iron oxide | Sodium carbonate/citric acid (35/65) | Sorbitol | Cremophor A25 ® |
|---|---|---|---|---|
| a | 80 | 10 | 10 | 0 |
| b | 80 | 10 | 9 | 1 |
| c | 80 | 10 | 6.66 | 3.33 |
| d | 80 | 10 | 2.5 | 7.5 |

Cremophor A25 ® is formed from oxyethylenated (25 OE) cetylstearyl alcohol.

The pigments used in this example are red iron oxides in accordance with those used in Example 1.

The solid anhydrous compositions formed essentially from colouring particles in accordance with the invention thus obtained are then mixed as described below with demineralized water at room temperature, so as to observe the self-dispersing properties of the pigments they contain.

To do this, they are firstly introduced with stirring into a flask containing 150 ml of deionized water, at a pigment concentration of 0.01% by weight relative to the total weight of the solution obtained.

The spontaneous dispersion of the pigments is then observed over time, for 5 minutes, at regular intervals, and especially at 1, 5, 10, 20 and 30 seconds, and then at 1 and 5 minutes.

In parallel, particle size measurements are performed using a Malvern Mastersizer 2000 laser granulometer.

The introduction of the solid anhydrous compositions formed essentially from colouring particles in accordance with the invention is then performed in demineralized water, with stirring.

The measurement is taken after a waiting time of 5 minutes.

The table below collates the results obtained.

The solid anhydrous compositions formed solely from colouring particles in accordance with the invention which have good self-dispersibility properties, i.e. which induce a gradual coloration of water, are indicated IC (Intense Coloration) or WC (Weak Coloration), and those that show no capacity for spontaneous dispersion are indicated UC (Uncoloured).

The mean diameter of the pigments (d(0.5) in µm), once dispersed, is also indicated.

|   | Cremophor A25 ® | d(0.5) in µm | Self-dispersibility |
|---|---|---|---|
| a | 0 | 1.62 | UC |
| b | 1 | 1.27 | WC |
| c | 3.33 | 0.85 | IC |
| d | 7.5 | 0.66 | IC |

The results obtained thus confirm that the presence of Cremophor A 25® is essential for obtaining good spontaneous wettability properties of the colouring particles formed solely from the anhydrous compositions tested, and especially from pigments.

In the context of this example, it is observed that a minimum concentration of about 1% by weight of Cremophor A 25® relative to the total weight of the colouring particles in accordance with the invention is beneficial to better wetting of the pigments contained in the said solid anhydrous composition formed solely from colouring particles in accordance with the invention, and thus to more intense colour development.

The efficacy of the dispersion is also reflected by a small particle size of the pigments, especially less than 1 µm, after only a few minutes in water. This particle size is compatible with satisfactory colour development.

EXAMPLE 3

Comparative Example with Respect to the Content of Effervescent System

Four compositions e, f, g and h formed solely from colouring particles in accordance with the invention and as defined in the table below are prepared according to the protocol defined in the description.

|   | Red iron oxide | Sodium carbonate/citric acid (35/65) | Sorbitol | Cremophor A25 ® |
|---|---|---|---|---|
| e | 65 | 25 | 6.66 | 3.33 |
| f | 75 | 15 | 6.66 | 3.33 |
| g | 80 | 10 | 6.66 | 3.33 |
| h | 85 | 5 | 6.66 | 3.33 |

The pigments used in this example are red iron oxides in accordance with those used in Example 1.

The solid anhydrous compositions thus obtained are then mixed with demineralized water at room temperature as described in Example 2, so as to observe the self-dispersion properties and the particle size of the pigments they contain.

|   | Sodium carbonate/citric acid (35/65) | d(0.5) in µm | Self-dispersibility |
|---|---|---|---|
| e | 25 | 0.71 | IC |
| f | 15 | 0.93 | IC |
| g | 10 | 0.85 | IC |
| h | 5 | 1.34 | WC |

The results obtained thus confirm that the presence of the effervescent system makes it possible to obtain good spontaneous wettability properties of the solid anhydrous composition formed solely from colouring particles in accordance with the invention, and especially of pigments.

A minimum concentration of effervescent system of about 8% to 10% by weight relative to the total weight of the colouring particles in accordance with the invention is beneficial to better wetting of the pigments, and thus to more intense colouring development.

Beyond this minimum concentration, the colour variation is not significant. The efficacy of the dispersion is greater and is reflected by a smaller particle size of the pigments, especially less than 1 μm, after only a few minutes in water. This particle size is compatible with satisfactory colour development.

Additional tests were performed in emulsion, by dispersing the said solid anhydrous compositions formed solely from colouring particles in accordance with the invention, with gentle manual stirring, into a care cream in accordance with Example 4.2.2 below, such that the product of the two compositions comprised 10% by weight of pigments, which represents a standard pigment content in a foundation.

These tests showed that beyond 20% by weight of effervescent system relative to the total weight of the said colouring particles in accordance with the invention, the presence of foam may be detected at the surface of the product obtained, especially associated with the evolution of gas during the effervescence, which is not desirable for the user.

EXAMPLE 4

Illustration of Products in Accordance with the Invention 4.1: Examples of First Composition Formed Solely from Colouring Particles in Accordance with the Invention P1 to P4 as defined in Example 1 are used. They are used alone or as a mixture.

4.2: Examples of Second Composition 4.2.1: Composition of a W/O Foundation

| Phase | Starting material | Weight % |
|---|---|---|
| A1 | Cetyl PEG/PPG-10/1 Dimethicone (ABIL EM 90 from Evonik Goldschmidt) | 0.80 |
| | Polyglyceryl-4 Isostearate (Isolan GI 34 from Evonik Goldschmidt) | 0.60 |
| | PEG-10 Dimethicone (KF 6017 from Shin-Etsu) | 5.00 |
| | Dimethicone | 5.85 |
| | Isohexadecane | 7.00 |
| A2 | Hectorite | 1.60 |
| A3 | Cyclopentasiloxane | 24.40 |
| A4 | Fluorinated iron oxides and titanium dioxide | 12.00 |
| B | Water | 36.75 |
| C | Mica | 2.00 |
| | Crosslinked polymethyl methacrylate polymer | 4.00 |

The starting materials of phase A1 are mixed together and homogenized with stirring at room temperature.

The starting materials of phase A2 are poured in gently with continued stirring at room temperature, until the said starting materials of phase A2 have totally dispersed.

Slurrying of phase A4 is then performed with a portion of phase A3, and the slurry thus obtained is ground using a 3-roll mill (3 times). Phases A4 and A3 are then added to the mixture of phases A1 and A2, with stirring in the manufacturing tank.

Phase B is then added with Moritz stirring at 1500 rpm, and the mixture is homogenized until an emulsion is obtained with cooling. Finally, the starting materials of phase C are added, so as to obtain a foundation of beige shade.

4.2.2: O/W Care Cream

| Phase | Starting material | Weight % |
|---|---|---|
| A1 | PEG-20 Stearate | 0.80 |
| | Glyceryl stearate (and) PEG-100 stearate (Arlacel 165 from the company Croda) | 2.00 |
| | Cetyl alcohol | 0.50 |
| | Stearyl alcohol | 0.50 |
| | Stearic acid | 3.00 |
| | Myristyl myristate | 2.00 |
| | Liquid paraffin | 6.15 |
| | Cera alba | 1.00 |
| | Shea butter (*Butyrospermum parkii*) | 2.00 |
| A2 | Cyclohexasiloxane | 10.64 |
| | Acrylate copolymer | 0.20 |
| B | Glycerol | 7.00 |
| | Disodium EDTA | 0.10 |
| | Water | 62.06 |
| | Triethanolamine | 0.15 |
| C | Acrylamide/sodium acryloyldimethyltaurate (and) isohexadecane (and) polysorbate 80 copolymer | 1.90 |

The various starting materials of phase B are mixed together and homogenized at room temperature until completely dissolved.

Since the presence of glycerol may be detrimental to the speed of the operation, this compound may also be added once the mixing of the other starting materials has been performed.

The starting materials of phase A1 are then added and the mixture thus obtained is heated to 72° C. until melting and dissolution are complete.

The mixture is then cooled to 65° C.

The starting materials of phase A2 are added while maintaining a constant temperature of the mixture at 62° C. and homogenizing until the acrylate copolymer has correctly dispersed, so as especially to avoid any setting on the walls.

The starting material of phase C is then added and the mixture is homogenized until the gel has fully dispersed with cooling to room temperature and until an emulsion is obtained.

4.2.3: O/W Care Cream

| Phase | Starting material | Weight % |
|---|---|---|
| A | Sorbitan tristearate | 0.90 |
| | PEG-40 stearate | 2.00 |
| | Cetyl alcohol | 4.00 |
| | Glyceryl stearate | 5.00 |
| | Cyclohexasiloxane | 8.00 |
| | Squalane | 13.60 |
| B | Disodium EDTA | 0.05 |
| | Glycerol | 7.00 |
| | Sodium hydroxide | 0.03 |
| | Water | 40.97 |
| C1 | Acrylate copolymer | 0.30 |
| C2 | Acrylamide/sodium acryloyldimethyltaurate (and) isohexadecane (and) polysorbate 80 copolymer | 1.30 |
| | Water | 16.85 |

The starting materials of phase B are mixed together and homogenized at room temperature until the sodium hydroxide has completely dissolved.

The starting materials of phase A are added and the mixture thus obtained is heated to 72° C., until melting and dissolution of the various compounds is complete.

The mixture is then cooled to 65° C. with continued homogenization of the mixture so as especially to avoid any setting on the walls.

The starting material of phase C1 is then added, followed by the starting materials of phase C2.

The mixture is homogenized until dispersion of the gel is complete with cooling to room temperature and until an emulsion is obtained.

4.2.4: Pulverant Care Composition Containing an Aqueous Phase

| Starting material | Weight % |
| --- | --- |
| Silica dimethyl silylate (Aerosil R812 (S), Evonik) | 5 |
| Xylisorb 90 (Xylitol) | 1 |
| Butylene glycol | 5 |
| Sodium citrate | 0.5 |
| Potassium sorbate | 0.45 |
| Microfine (copolyamide 6/12) | 5 |
| Stay C50 (sodium ascorbyl phosphate) | 6 |
| Water | 77.05 |

The starting materials of the above table are mixed together by simple mechanical stirring. The mixture thus obtained is in the form of a pulverant composition.

4.3: Examples of Extemporaneous Preparation 4.3.1: First Composition Formed Solely from Colouring Particles in Accordance with the invention in combination with a W/O foundation 2% of composition A as described in Example 1, in which the pigment is red iron oxide, are added to 98% of a W/O foundation composition of Example 4.2.1 above.

The product of these two compositions is mixed together with manual stirring for 1 minute.

The shade of the foundation thus obtained changes when composition A is introduced and becomes pinky-beige.

4.3.2: First Composition Formed Solely from a Mixture of Colouring Particles in Accordance with the Invention in Combination with an O/W Care Cream 1.50% of P1, 0.71% of P2, 0.29% of P3 and 10% of P4, defined above, are simultaneously introduced into 87.50% by weight of a care cream of Example 4.2.2 above.

Manual mixing is performed using a spatula until a pigmented cream of uniform beige colour is obtained.

The product thus obtained is uniform in colour and the dispersion of the pigments is regular and fine. It shows good cosmetic properties and good ease of application. The makeup effect is natural, it unifies in transparency and leaves the skin moisturized.

4.3.3: First Composition Formed Solely from a Mixture of Colouring Particles According to the Invention in Combination with a Care Cream 1.50% of P1, 0.71% of P2, 0.29% of P3 and 10% of P4, defined above, are simultaneously introduced into 87.50% by weight of a care cream of Example 4.2.3 above.

The introduction by manual stirring of the various colouring particles into the care cream shows that the pigmentary dispersion is uniform and easy, without any lumps of pigment on application. The application of the product is slippery, the film is uniform and the coverage is light.

4.3.4: First Composition Formed Solely from a Mixture of Colouring Particles in Accordance with the Invention in Combination with a Care Cream The end of a wooden or plastic stick is impregnated with butylene glycol and rolled in a mixture comprising 12% of P1, 5.68% of P2, 2.32% of P3 and 80% of P4, defined above, the said mixture being prepared beforehand using a Novamix 1 L mixer/granulator from RPA Process Technologies.

The stick rolling operation is repeated until a ball of the desired size is obtained.

The stick is then dried in an oven at 45° C. for 24 hours.

This tool is then dipped into a dose of 1 gram of care cream of Example 4.2.2 above.

The colour development observed is immediate and uniform. The care cream takes a beige shade. The makeup effect is uniform on the skin and leaves a natural finish.

4.3.5: First Composition Formed Solely from a Mixture of Colouring Particles in Accordance with the Invention in Combination with a Pulverant Care Composition Containing an Aqueous Phase Preliminary mixing of 12% of P1, 5.68% of P2, 2.32% of P3 and 80% of P4, defined above, is performed using a Novamix 1 L mixer/granulator from RPA Process Technologies.

0.15 g of this mixture is then introduced into 1 g of a composition of Example 4.2.4 above.

The said product is prepared on the back of the hand, by simple mechanical stress. The water contained in the powder is released under mechanical pressure and allows wetting of the pigments. The product obtained is a pigmented aqueous cream which, when applied to the skin, gives a natural and uniform makeup result.

4.3.6: First "Simplex" Composition in Combination with a Care Cream

Preliminary mixing of 8.57% of P1, 4.06% of P2, 1.66% of P3 and 57.11% of P4, defined above, and 28.6% of methyl methacrylate crosslinked polymer sold under the name Micropearl M305 by the company SEPPIC, is performed using a Novamix 1 L mixer/granulator from RPA Process Technologies.

The simplex composition thus obtained is then mixed with a care composition as defined in Example 4.2.2 above.

The cosmetic composition thus obtained is coloured in a beige shade, and produces a matt result, of natural and uniform colour on the skin.

4.3.7: First "Complex" Composition in the Form of a Self-Emulsifying Powder in Water Preliminary preparation of composition P5 is performed as illustrated by the table below.

Composition P5

| Phase | Starting material | % |
| --- | --- | --- |
| A | Starch carboxymethyl ether, sodium salt (Covagel) | 39 |
|   | Hollow polymethyl methacrylate microspheres (Covabead LH 85) | 20.025 |
| B | Mixture of oxyethylenated (26 OE) oxypropylenated (26 OP) butyl alcohol, oxyethylenated (40 OE) hydrogenated castor oil in water (solubilizer LRI) | 3.225 |
|   | Deodorized macadamia nut oil | 12.75 |
| C | Composition P1 | 3 |
|   | Composition P2 | 1.42 |
|   | Composition P3 | 0.58 |
|   | Composition P4 | 20 |
| TOTAL |   | 100 |

Phase A is prehomogenized using a mixer (household mini-mixer). Phase B is then added to the pulverant mixture previously obtained and the whole is rehomogenized in the mixer. A white preparation in powder form is then obtained. Phase C is finally incorporated and homogenized with phases A+B in the mixer.

50% of composition P5 and 50% of demineralized water are then placed in contact and mixed together, at room temperature.

The product thus obtained is a creamy uniform foundation of beige shade. Application to the skin is fresh and gives a uniform makeup result.

The invention claimed is:
1. Cosmetic product comprising at least:
a first anhydrous cosmetic composition comprising at least colouring particles that are solid at room temperature and atmospheric pressure, each of the particles comprising:
  at least one hydrophilic dyestuff in a content ranging from 60 to 95% by weight relative to total weight of the particles,
  at least one effervescent system in a content ranging from 1 to 20% by weight relative to the total weight of the particles,
  at least one hydrophilic binder, and
  at least one dispersant that is different from the hydrophilic binder; and
a second composition comprising at least one aqueous phase.

2. Cosmetic product according to claim 1, comprising at least:
(i) the first anhydrous cosmetic composition comprising colouring particles, each of the particles comprising at least the hydrophilic dyestuff(s), the effervescent system(s), the hydrophilic binder(s) and the dispersant(s) in a total content of greater than or equal to 98% by weight relative to the total weight of the first composition, and the second composition comprising at least one aqueous phase in the form of a cosmetic composition, or
(ii) the first anhydrous cosmetic composition comprising colouring particles, each of the particles comprising at least the hydrophilic dyestuff(s), the effervescent system(s), the hydrophilic binder(s) and the dispersant(s) in a total content of greater than or equal to 85% by weight relative to the total weight of the first composition and at least one non-aqueous binder, and the second composition comprising at least one aqueous phase in the form of a cosmetic composition, or
(iii) the first anhydrous cosmetic composition comprising colouring particles, each of the particles comprising at least the hydrophilic dyestuff(s), the effervescent system(s), the hydrophilic binder(s) and the dispersant(s) in a total content of greater than or equal to 20% by weight relative to the total weight of the first composition, at least one coloured and/or uncoloured pulverant material, and optionally at least one non-aqueous binder, and the second composition comprising at least one aqueous phase in the form of a cosmetic composition, or
(iv) the first anhydrous cosmetic composition comprising colouring particles, each of the particles comprising at least the hydrophilic dyestuff(s), the effervescent system(s), the hydrophilic binder(s) and the dispersant(s) in a total content of greater than or equal to 4% by weight relative to the total weight of the first composition, at least one non-aqueous binder, at least one coloured and/or uncoloured pulverant material, and at least one additional ingredient selected from the group consisting of surfactants, gelling agents, polymers, fibres, chelating agents, active agents, fragrances, and mixtures thereof, and the second composition comprising at least water in a content of greater than 80% by weight relative to the total weight of the second composition.

3. Cosmetic product according to claim 1, wherein:
the hydrophilic dyestuff is selected from the group consisting of:
  water-soluble dyes;
  pigments;
  nacres;
  particles with a metallic glint;
  diffracting pigments;
  goniochromatic colouring agents; and
  mixtures thereof;
the particles with a metallic glint are selected from the group consisting of:
  at least one metal and/or at least one metal derivative;
  particles comprising a monomaterial or multimaterial organic or mineral substrate at least partially covered with at least one layer with a metallic glint comprising at least one metal and/or at least one metal derivative; and
  mixtures thereof; and
the metal derivative is selected from the group consisting of titanium oxide, iron oxide, tin oxide, chromium oxide, barium sulphate, $MgF_2$, $CrF_3$ ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

4. Cosmetic product according to claim 2, wherein the solid colouring particles comprise from 65 to 90% by weight of hydrophilic dyestuff(s) relative to the total weight of the particles.

5. Cosmetic product according to claim 1, wherein the effervescent system is an acid/base couple.

6. Cosmetic product according to claim 1, wherein the solid colouring particles comprise from 5 to 15% by weight of effervescent system(s), relative to the total weight of the particles.

7. Cosmetic product according to claim 1, wherein the hydrophilic binder is solid at room temperature and atmospheric pressure.

8. Cosmetic product according to claim 1, wherein the hydrophilic binder is chosen from $C_4$-$C_{32}$ polyols and polyoxyethylenated ether.

9. Cosmetic product according to claim 1, wherein the solid particles comprise from 1% to 20% by weight of hydrophilic binder(s), relative to the total weight of the particles.

10. Cosmetic product according to claim 1, wherein the dispersant is selected from the group consisting of nonionic, anionic and cationic surfactants, and mixtures thereof, with an HLB of greater than 10.

11. Cosmetic product according to claim 10, wherein the dispersant is a nonionic surfactant with an HLB of greater than 10.

12. Cosmetic product according to claim 1, wherein the solid colouring particles comprise from 0.1% to 20% by weight of dispersant(s), relative to the total weight of the particles.

13. Cosmetic process comprising:
providing at least a first anhydrous composition as defined in claim 1;
(ii) mixing at least part of the first composition with at least a second composition comprising at least one aqueous phase; and
(iii) applying at least part of the mixture obtained in (ii) to the surface of a keratin material.

14. A method for tinting or modifying a colour property of a second composition comprising at least one aqueous phase, comprising adding to the second composition a first anhydrous cosmetic composition comprising at least colouring particles that are solid at room temperature and atmospheric pressure, each of the particles comprising:
- at least one hydrophilic dyestuff in a content ranging from 60% to 95% by weight relative to a total weight of the particles,
- at least one effervescent system in a content ranging from 1% to 20% by weight relative to the total weight of the particles,
- at least one hydrophilic binder, and
- at least one dispersant that is different from the hydrophilic binder.

* * * * *